United States Patent [19]

Finch et al.

[11] Patent Number: 4,940,702

[45] Date of Patent: Jul. 10, 1990

[54] CEPHEM COMPOUNDS

[75] Inventors: Stephen C. Finch; Michael J. Pearson, both of Betchworth, United Kingdom

[73] Assignee: Beecham Group p.l.c., England

[21] Appl. No.: 894,926

[22] Filed: Aug. 8, 1986

[30] Foreign Application Priority Data

Aug. 10, 1985 [GB] United Kingdom ............... 8520155
Feb. 6, 1986 [GB] United Kingdom ............... 8602956

[51] Int. Cl.$^5$ ............... C07D 501/57; A61K 31/545
[52] U.S. Cl. ............................... 514/201; 540/221
[58] Field of Search ............... 540/221, 225; 514/201

[56] References Cited

U.S. PATENT DOCUMENTS 4,539,149  9/1985  Mulne ........................... 540/221
4,555,363  11/1985 Mulne ........................... 540/221
4,609,652  9/1986  Milner .......................... 514/194
4,670,431  6/1987  Milner .......................... 514/194
4,684,639  8/1987  Buoton et al. ................. 540/221

FOREIGN PATENT DOCUMENTS 0114750  8/1984  European Pat. Off. .

Primary Examiner—Nicholas S. Rizzo
Attorney, Agent, or Firm—Jacobs & Jacobs

[57] ABSTRACT

β-Lactam antibiotics are disclosed which have the formulae (Ia) or pharmaceutically acceptable salts or pharmaceutically acceptable in vivo hydrolysable esters thereof:

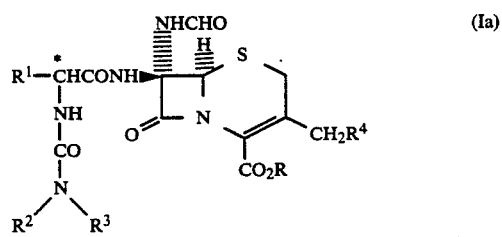

wherein $R^1$ is phenyl, substituted phenyl, cyclohexenyl, cyclohexadienyl, or an optionally substituted 5- or 6-membered heterocyclic ring containing up to three hetero-atoms selected from oxygen, sulphur or nitrogen; $R^2$ is hydrogen or optionally substituted $C_{1-6}$ alkyl; $R^3$ is an optionally substituted 5- or 6- membered heterocyclic group containing one or two nitrogen heteroatoms; or $R^2$ and $R^3$ together with the nitrogen atom to which they are attached form an optionally substituted 5- or 6- membered heterocyclic group contaning one or two nitrogen heteroatoms; $R^4$ is a substituted pyridinium group; and $CO_2R$ is carboxy or a carboxylate anion; and also the use thereof.

Processes for the preparation of the compounds are disclosed together with intermediates for use therein.

15 Claims, No Drawings

CEPHEM COMPOUNDS

This invention relates to a class of novel β-lactam derivatives, which have antibacterial activity and are of value in the treatment of infections in animals, especially mammals including man, caused by a wide range of organisms, particularly Gram-negative organisms. The invention also relates to a process for the preparation of such compounds, intermediates for use in the preparation of the compounds and to pharmaceutical compositions comprising the antibacterially active compounds.

European Patent Application Number 82303821.1 (Publication Number 0071395) discloses a class of β-lactam antibiotics having an α-formamido (formamidyl) substituent on the carbon atom adjacent to the carbonyl group of the β-lactam ring. It has now been found that, within this class of compounds, there exist cephalosporin derivatives with outstanding antibacterial properties.

Accordingly the present invention provides 7α-formamido cephalosporins of formula (I) or a salt thereof:

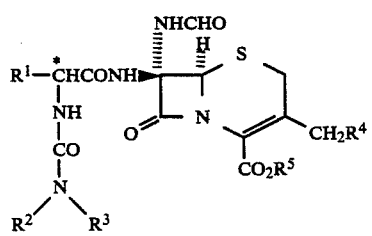

in which $R^1$ is phenyl, substituted phenyl, cyclohexenyl, cyclohexadienyl, or a 5- or 6-membered heterocyclic ring containing up to three hetero-atoms selected from oxygen, sulphur or nitrogen, optionally substituted with hydroxy, amino, halogen, substituted amino, or $C_{1-6}$ alkoxy; $R^2$ is hydrogen or an optionally substituted $C_{1-6}$ alkyl group; and $R^3$ is an optionally substituted 5- or 6-membered heterocyclic group containing one or two nitrogen heteroatoms; or $R^2$ and $R^3$ together with the nitrogen atom to which they are attached form an optionally substituted five- or six-membered heterocyclic group containing one or two nitrogen heteroatoms; $R^4$ is a substituted pyridinium group of formula (a), (b) or (c):

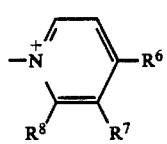

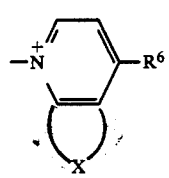

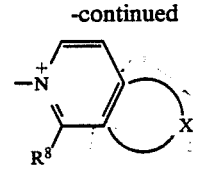

wherein $R^6$ is halogen; trifluoromethyl; $C_{1-6}$ alkyl optionally substituted by up to two groups selected from hydroxy, $C_{1-6}$ alkoxy, halogen, carboxy, cyano, carbamoyl, amino, $C_{1-6}$ alkyloxycarbonylamino, arylthio, $-SO_3^-$ and oxo; $C_{2-6}$ alkenyl; $C_{2-6}$ alkynyl; $C_{3-7}$ cycloalkyl; $C_{3-7}$ cycloalkenyl; $C_{3-7}$ cycloalkyl $C_{1-6}$ alkyl; cyano; $C_{1-6}$ alkylthio; arylthio; sulphonamido; arylamino; arylamido; $C_{1-6}$ alkoxy; carbamoyl; N-hydroxycarbamoyl; formyl; hydroximinomethyl; $C_{1-6}$ alkylcarbonyl; aryl; optionally substituted heterocyclyl; amino; nitro; hydroxy; $C_{1-6}$ alkylamido; di($C_{1-6}$ alkyl)amido; $C_{1-6}$ alkylcarbonyloxy; arylcarbonyloxy; carboxy; $C_{1-6}$ alkoxycarbonyl; aryloxycarbonyl; $C_{1-6}$ alkoxycarbonyloxy; aryloxycarbonyloxy; aryloxy; aralkyloxy; arylcarbonyl; $C_{1-6}$ alkylamino; or di($C_{1-6}$)alkylamino: $R^7$ and $R^8$ are as defined for $R^6$ and $R^6$, $R^7$, and $R^8$ are the same or different; or one or two of the groups $R^6$, $R^7$ or $R^8$ represents hydrogen; X represents a group $-CH_2X^1CH_2-$ wherein $X^1$ is O, S, or a group $NR^{22}$ wherein $R^{22}$ is H or $C_{1-6}$ alkyl; or X represents a group $-(CH_2)_n-$ wherein n is an integer having the value 2, 3 or 4; or a group of formula $-(CH_2)_p-CH=CH-(CH_2)_q-$ wherein p and q are integers, which may be the same or different, each having the value 0, 1 or 2, and wherein p+q has the value 1 to 3; or a group of formula $-O(CH_2)_mO-$ wherein m is an integer having the value 1 or 2; or X together with the bond in the ring to which it is joined forms an optionally substituted 6-membered aromatic carbocyclic ring or an optionally substituted 5- or 6-membered heteroaromatic ring containing from one to three heteroatoms selected from oxygen, nitrogen and sulphur; and $CO_2R^5$ is carboxy or a carboxylate anion, or the group $R^5$ is a readily removable carboxy protecting group.

The compounds of the invention of formula (I) are quaternary salts and the positive charge on the pyridinium moiety $R^4$ must always be balanced by a counter anion. The counter anion may be present on a negatively charged group within the molecule, such as the carboxylate anion $CO_2R^5$, or the counter anion may be present as an external, inorganic or organic anion.

In compounds of formula (I), the formamido group can exist in conformations wherein the hydrogen atoms of the —NH—CHO moiety are cis- or trans-; of these the cis conformation normally predominates.

When used herein the term "aryl" includes phenyl and naphthyl optionally substituted with up to five fluorine, chlorine, $C_{1-6}$ alkyl, $C_{1-6}$ alkoxy, halo $(C_{1-6})$alkyl, hydroxy, amino, carboxy, $C_{1-6}$ alkoxycarbonyl, aryloxycarbonyl, $C_{1-6}$ alkoxycarbonyl$(C_{1-6})$alkyl, nitro, aryloxycarbonyloxy, aryl $C_{1-6}$ alkyloxycarbonyloxy, $C_{1-6}$ alkyloxycarbonyloxy, $C_{1-6}$ alkylcarbonyloxy, arylcarbonyloxy, aryl $C_{1-6}$ alkylcarbonyloxy, or aryl $C_{1-6}$ alkyloxycarbonyl groups.

The term "heterocyclyl" herein denotes single or fused aromatic or non-aromatic heterocyclic rings, said rings containing up to four hetero atoms selected from oxygen, nitrogen and sulphur and being optionally substituted with up to three halogen, $C_{1-6}$ alkyl, $C_{1-6}$ alkoxy, halo$(C_{1-6})$alkyl, hydroxy, amino, carboxy, $C_{1-6}$ alkoxycarbonyl, $C_{1-6}$ alkoxycarbonyl($C_{1-6}$)alkyl, aryl, or oxo groups. Suitably the heterocyclic ring comprises from 4 to 7 ring atoms, preferably 5 or 6 atoms. Depending on the nature of the heterocyclyl group, certain compounds within formula (I) may occur in two or more tautomeric forms; these are included within the scope of the present invention.

The term "halogen" refers to fluorine, chlorine, bromine and iodine.

The carbon atom marked * in formulae herein is asymmetric and thus compounds of formula (I) may exist as two optically active diastereoisomers. In general the isomer prepared from the D-side chain exhibits the highest antibacterial activity and accordingly the D compound or the DL mixtures are preferred, with the D compound being particularly preferred.

The compounds of formula (I) with the preferred D-sidechain can be separated from a mixture of both diastereoisomers by conventional methods, or prepared from intermediates that bear a D- side chain.

Suitably the substituted phenyl group for $R^1$ is a phenyl group substituted with up to three groups selected from $C_{1-6}$ alkyl, phenyl, halogen, amino, nitro, hydroxy, $C_{1-6}$ alkylamido, carbamoyl, carboxy, $C_{1-6}$ alkoxycarbonyl, aryloxycarbonyl, halo ($C_{1-6}$) alkyl, hydroxy($C_{1-6}$)alkyl, oxo($C_{1-6}$)alkyl, $C_{1-6}$ alkylcarbonyl, arylcarbonyl, $C_{1-6}$ alkylamino, di($C_{1-6}$) alkylamino, or sulphonamido, the amino and hydroxy groups being optionally protected.

The optional protecting groups for any hydroxy or amino groups attached to a phenyl ring in $R^1$ are suitably readily cleaved and include in vivo hydrolysable groups as well as groups which may be cleaved by conventional chemical or enzymatic methods.

A comprehensive discussion of the ways in which hydroxy and amino groups may be protected and methods for cleaving the resulting protected derivatives are given, for example, in "Protective Groups in Organic Synthesis" by T. W. Greene (Wiley-Interscience, New York, 1981). Particularly suitable protecting groups include those which, when protecting a 3- and/or 4-hydroxy group in $R^1$ afford esters or carbonates (both of which may be in vivo hydrolysable), ethers (including silyl ethers) and ketals (for example tetrahydropyranyloxy derivatives, sometimes described as 'THP ethers').

When amino protection is required, for example when $R^1$ is 3- or 4-aminophenyl, suitable protecting groups include, for example, those that afford amides and carbamates.

When two hydroxy groups are attached to the phenyl ring in $R^1$, for example, when $R^1$ is 3,4-dihydroxyphenyl, it will be understood that one or both of the hydroxy groups may be protected. When both hydroxy groups are protected it will be understood that a different protecting group may be used for each hydroxy group, although, more conveniently, the protecting groups used will be the same.

Examples of suitable hydroxy protecting groups, for example for a 3- and/or 4-hydroxy group in $R^1$ include formyl and optionally substituted $C_{1-6}$ alkylcarbonyl and arylcarbonyl groups such as acetyl, chloroacetyl, dichloroacetyl and benzoyl; optionally substituted $C_{1-6}$ alkoxycarbonyl and aryl $C_{1-6}$ alkoxycarbonyl, for example ethoxycarbonyl, trimethylsilylethoxycarbonyl, benzyloxycarbonyl and 4-nitrobenzyloxycarbonyl; and optionally substituted $C_{2-6}$ alkenyloxycarbonyl such as allyloxycarbonyl.

Further examples of suitable hydroxy protecting groups, for example for a 3- and/or 4-hydroxy group in $R^1$ include aryl, aryl $C_{1-6}$ alkyl, optionally substituted $C_{1-6}$ alkyl, optionally substituted $C_{2-6}$ alkenyl, optionally substituted $C_{3-7}$ cycloalkyl, and silyl groups.

Some examples of optional substituents in protecting groups mentioned hereinabove as being optionally substituted include up to three groups (which may be the same or different) chosen from halogen, hydroxy, $C_{1-6}$ alkoxy, $C_{1-6}$ alkylthio, cyano, nitro, carboxy, carboxylic acid $C_{1-6}$ alkyl ester, carbamoyl, amino, mono ($C_{1-6}$) alkylamino, and di ($C_{1-6}$) alkylamino.

Preferred alkyl protecting groups for a 3- and/or 4-hydroxy group in $R^1$ include, for example, methyl or ethyl, optionally substituted with ($C_{1-6}$) alkoxy or ($C_{1-6}$) alkylthio, for example with methoxy, ethoxy, or methylthio. Further useful protecting groups are methoxyethoxymethyl and (trimethylsilyl)ethoxymethyl. In addition, when $R^1$ is 3,4-dihydroxyphenyl, the hydroxy groups may be protected by an alkylene bridge so that $R^1$ becomes, for example, 3,4-methylenedioxyphenyl, 3,4-ethylenedioxyphenyl, or 3,4-[1,1-dimethyl- (methylenedioxy)]phenyl.

Preferred aryl $C_{1-6}$ alkyl protecting groups for a 3- and/or 4-hydroxy group in Rl include benzyl and 4-nitrobenzyl.

Preferred silyl protecting groups may be substituted with $C_{1-6}$ alkyl and/or phenyl groups and include, for example, trimethylsilyl, t-butyldimethylsilyl, t-butyldiphenylsilyl, triethylsilyl, isopropyldimethylsilyl, triphenylmethyldimethylsilyl and the like. The resulting silyl ethers may be cleaved by methods known in the art, such as those described by T. W. Greene (loc. cit.) or by M. Lalonde and T. H. Chan in Synthesis, 1985 (September), pages 817–845 and references therein.

A particularly preferred hydroxy protecting group is acetyl.

From the foregoing it may be seen that in one favoured group of compounds according to the invention the group $R^1$ is phenyl, 3-hydroxyphenyl, 3-($C_{1-6}$ alkylcarbonyloxy)phenyl, 3-(aryl $C_{1-6}$ alkyloxycarbonyloxy)phenyl, 4-hydroxyphenyl, 4-($C_{1-6}$ alkylcarbonyloxy)phenyl, 4-(aryl $C_{1-6}$ alkyloxycarbonyloxy)phenyl, 3,4-dihydroxyphenyl, 3,4-di($C_{1-6}$ alkylcarbonyloxy)-phenyl, 3,4-di(aryl $C_{1-6}$ alkyloxycarbonyloxy)phenyl, 2-halo-4,5-di($C_{1-6}$ alkylcarbonyloxy)phenyl, 2-halo-4,5-dihydroxyphenyl, 2-halo-4,5-di(aryl $C_{1-6}$ alkyloxycarbonyloxy)phenyl, 3,4-methylenedioxyphenyl, 2-thienyl, or 2-furyl.

Particularly preferred groups $R^1$ are phenyl, 3,4-dihydroxyphenyl, 3,4-diacetoxyphenyl, 2-chloro-4,5-diacetoxyphenyl, 2-chloro-4,5-dihydroxyphenyl, 3,4-methylenedioxyphenyl, 2-thienyl, and 2-furyl.

Suitable substituents for the 5- or 6-membered heterocyclic group of $R^3$ or $R^2$ and $R^3$ together include $C_{1-6}$ alkyl, $C_{2-6}$ alkenyl, $C_{2-6}$ alkynyl, $C_{3-7}$ cycloalkyl or $C_{4-8}$ cycloalkenyl groups; aryl; oxo; the hydroxy group optionally substituted by $C_{1-6}$ alkyl, $C_{2-6}$ alkenyl, $C_{3-7}$ cycloalkyl, phenyl, pyridyl, pyrimidyl, or benzyl; mercapto; $C_{1-6}$ alkylthio; $C_{1-6}$ alkylsulphonyl; or the amino group optionally substituted by up to two $C_{1-6}$ alkyl, $C_{2-6}$ alkenyl, $C_{3-7}$ cycloalkyl, aryl, or benzyl groups. Alternatively two substituents on the ring may form the residue of a 5- or 6-membered carbocyclic ring or the residue of a 5- or 6-membered heterocyclic ring containing up to three hetero atoms selected from oxygen, nitrogen and sulphur.

Suitable substituents for $R^6$ include hydrogen, $C_{1-6}$ alkyl, $C_{1-6}$ alkoxy, carbamoyl, phenyl, pyridyl, (2-N-t-butoxycarbonylamino-2-carboxy)ethyl, $C_{3-7}$ cycloalkyl, $C_{1-6}$ alkylthio or $C_{1-6}$ alkylsulphonate Preferably $R^6$ is hydrogen, methyl, ethyl, t-butyl, methoxy, carbamoyl, phenyl, 2-pyridyl, (2-N-t-butoxycarbonylamino-2-carboxy)ethyl, cyclopropyl, n-propyl, iso-propyl, or $-CH_2CH_2SO_3^-$.

Suitable substituents for $R^7$ include hydrogen, $C_{1-6}$ alkyl, $C_{3-7}$ cycloalkyl, hydroxy $C_{1-6}$ alkyl, $C_{1-6}$ alkylcarbonyl, $C_{1-6}$ alkoxy, halo, or carbamoyl.

Preferably $R^7$ is hydrogen, methyl, ethyl, hydroxymethyl, hydroxypropyl, acetyl, chloro, methoxy, or carbamoyl.

Suitable substituents for $R^8$ include hydrogen, $C_{1-6}$ alkyl, and $C_{3-7}$ cycloalkyl.

Preferably $R^8$ is hydrogen or ethyl.

Suitably X is a group of formula $-(CH_2)_n-$ wherein n is 3 or 4, preferably 3.

Another suitable group for X is that of the formula:

Preferably $R^4$ is 4-ethylpyridinium, 4-cyclopropylpyridinium, or the 2,3-cyclopentenopyridinium group of formula:

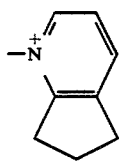

Included within the scope of readily removable carboxy protecting groups for $R^5$ are, for example, ester groups including pharmaceutically acceptable in vivo hydrolysable ester groups. It will be appreciated that also included within the scope of the invention are salts and carboxy-protected derivatives, including in vivo hydrolysable esters, of any carboxy groups that may be present as optional substituents in compounds of formula (I). Also included within the scope of the invention are acid addition salts of any amino or substituted amino groups that may be present as optional substituents in compounds of formula (I).

Since the β-lactam antibiotic compounds of the present invention are intended for use in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

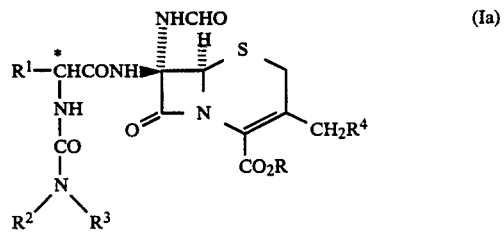

wherein $R^1$, $R^2$, $R^3$, $R^4$ and * are as defined for formula (I) and the group $CO_2R$ is carboxy or a carboxylate anion.

Non-pharmaceutically acceptable salts of the compound of formula (I) are primarily of use as intermediates in the preparation of a compound of formula (Ia) or a pharmaceutically acceptable salt or pharmaceutically acceptable in vivo hydrolysable ester thereof. Salts within compounds of formula (I) may be prepared by salt exchange in conventional manner.

Similarly, non-pharmaceutically acceptable carboxy-protected derivatives of formula (I) for example certain compounds of formula (I) wherein $R^5$ is a readily removable carboxy protecting group, may be used as intermediates in the preparation of pharmaceutically acceptable compounds of formula (Ia) or pharmaceutically acceptable salts or pharmaceutically acceptable in vivo hydrolysable esters thereof.

From the foregoing, it will be appreciated that within the quaternary salts of the invention of the formula (I) and (Ia) there exist the sub-groups (Ib) and pharmaceutically acceptable salts and in vivo hydrolysable esters thereof; and (Ic) and in vivo hydrolysable esters thereof:

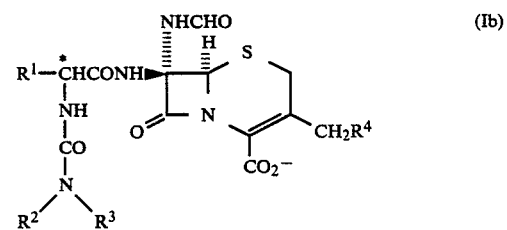

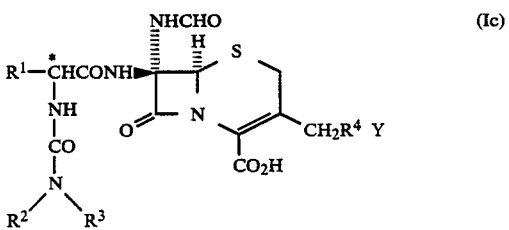

wherein $R^1$, $R^2$, $R^3$, $R^4$, and * are defined with respect to formula (I), and Y is a pharmaceutically acceptable inorganic or organic anion present in the appropriate stoicheiometric proportion to balance the positive charge on $R^4$.

In a preferred aspect of the invention, the compounds of formula (I) are betaines, i.e. may also be represented by the formula (Ib). (A betaine is defined as an uncharged species having isolated non-adjacent cationic and anionic sites, and not possessing a hydrogen atom bonded to the cationic site.)

When the compounds of the invention of formula (I) or (Ia) may be represented by the formula (Ic), the counter anion Y is suitably derived from an inorganic acid, preferably a mineral acid.

Thus, in formula (Ic), the anion Y may suitably be chloride, bromide, iodide, phosphate (i.e. $\frac{1}{3} PO_4^{3-}$) or sulphate (i.e. $\frac{1}{2} SO_4^{2-}$).

Preferably Y is chloride.

Conversion of betaines of sub-formula (Ib) into salts of sub-formula (Ic) and vice versa may readily be carried out by conventional methods. For example salts of the sub-formula (Ic) may be prepared from betaines of sub-formula (Ib) by treatment with a dilute mineral acid such as hydrochloric acid.

Quaternary salts within formula (Ic) may also be prepared by salt exchange in a conventional manner, for example by means of an ion-exchange resin.

Since the β-lactam antibiotic compounds of the present invention are intended for use in pharmaceutical compositions it will readily be understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical it will readily be understood that the substantially pure form is preferred as for the β-lactam antibiotic compounds. Preferably, whenever possible, the compounds of the present invention are obtained in crystalline form.

When some of the compounds of this invention are allowed to crystallise, or are recrystallised, from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Suitable readily removable carboxyl protecting groups for the group —CO$_2$R$^5$ include groups forming ester derivatives of the carboxylic acid, including in vivo hydrolysable esters. The derivative is preferably one which may readily be cleaved.

Suitable ester-forming carboxyl-protecting groups are those which may be removed under conventional conditions. Such groups for R$^5$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR$^{18}$ where R$^{18}$ is aryl or heterocyclic, or an in vivo hydrolysable ester radical such as defined below.

A carboxyl group may be regenerated from any of the above esters by usual methods appropriate to the particular R$^5$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

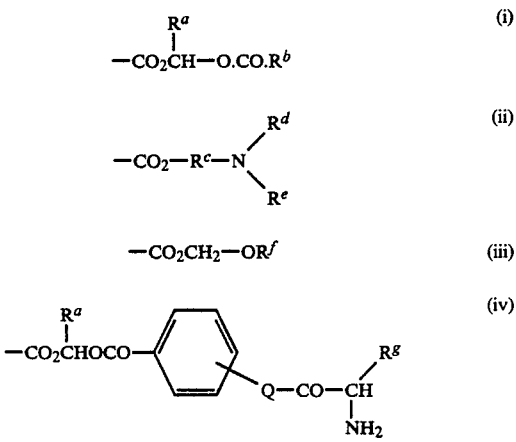

wherein R$^a$ is hydrogen, C$_{1-6}$ alkyl, C$_{3-7}$ cycloalkyl, methyl, or phenyl; R$^b$ is C$_{1-6}$ alkyl, C$_{1-6}$ alkoxy, phenyl, benzyl, C$_{3-7}$ cycloalkyl, C$_{1-6}$ alkyl C$_{3-7}$ cycloalkyl, 1-amino C$_{1-6}$ alkyl, or 1-(C$_{1-6}$ alkyl)amino C$_{1-6}$ alkyl; or R$^a$ and R$^b$ together form a 1,2-phenylene group optionally substituted by one or two methoxy groups; R$^c$ represents C$_{1-6}$ alkylene optionally substituted with a methyl or ethyl group and R$^d$ and R$^e$ independently represent C$_{1-6}$ alkyl; R$^f$ represents C$_{1-6}$ alkyl; R$^g$ represents hydrogen or phenyl optionally substituted by up to three groups selected from halogen, C$_{1-6}$ alkyl, or C$_{1-6}$ alkoxy; and Q is oxygen or NH.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

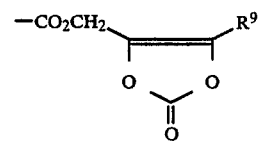

wherein R$^9$ is hydrogen, C$_{1-6}$ alkyl or phenyl.

One particularly preferred sub-group within the present invention provides a compound of formula (II) or a pharmaceutically acceptable salt or in vivo hydrolysable ester thereof:

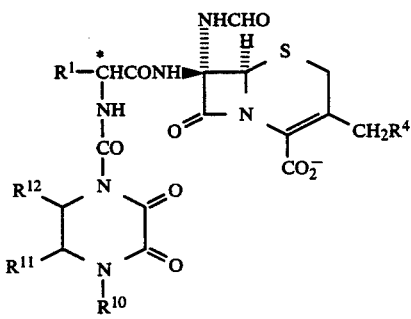

(II)

wherein $R^1$,* and $R^4$ are as defined with respect to formula (I) and $R^{10}$ represents hydrogen, $C_{1-8}$ alkyl, aryl, or aryl $C_{1-6}$ alkyl; $R^{11}$ and $R^{12}$ are the same or different and represent hydrogen, $C_{1-6}$ alkyl, halogen, amino, hydroxy, or $C_{1-6}$ alkoxy; or $R^{11}$ and $R^{12}$ form the residue of 5- or 6-membered carbocyclic ring or the residue of a 5- or 6-membered heterocyclic ring containing up to three hetero atoms selected from oxygen, nitrogen and sulphur.

Suitable $C_{1-6}$ alkyl groups for the groups $R^{10}$, $R^{11}$ and $R^{12}$ in formula (II) include methyl, ethyl, n- and iso-propyl, n-, sec-, iso- and tert-butyl.

Preferably $R^{10}$ is ethyl or 3-chlorophenyl.

Preferably $R^{11}$ and $R^{12}$ are hydrogen.

Most preferably $R^{10}$ is ethyl and $R^{11}$ and $R^{12}$ are both hydrogen.

Specific compounds within this invention include the following and pharmaceutically acceptable salts and in-vivo hydrolysable esters thereof:

7β-[D-2-[(4-Ethyl-2,3-dioxopiperazin-1-yl) carbonylamino]-2-phenylacetamido]-3-(4-ethylpyridinium) methyl-7α-formamido-ceph-3-em-4-carboxylate 3-(2,3-Cyclopentenopyridinium)methyl-7β-[D-2-(3,4-diacetoxyphenyl)-2-[(4-ethyl-2,3-dioxopiperazin-1-yl) carbonylamino]acetamido]-7α-formamido-ceph-3-em-4-carboxylate 3-(2,3-Cyclopentenopyridinium)methyl-7β-[D-2-(3,4-dihydroxyphenyl)-2-[(4-ethyl-2,3-dioxopiperazin-1-yl) carbonylamino]acetamido]-7α-formamido-ceph-3-em-4-carboxylate 7β-[D,L-2-[(4-Ethyl-2,3-dioxopiperazin-1-yl) carbonylamino]-2-(fur-2-yl)acetamido]-7α-formamido-3-(4-ethylpyridinium)methyl-ceph-3-em-4-carboxylate 7β-[D,L-2-[(4-Ethyl-2,3-dioxopiperazin-1-yl) carbonylamino]-2-(thien-2-yl)acetamido]-3-(4-ethylpyridinium)methyl-7α-formamido-ceph-3-em-4-carboxylate 7β-[D,L-2-[(4-Ethyl-2,3-dioxopiperazin-1-yl) carbonylamino]-2-(3,4-methylenedioxyphenyl)acetamido]-3-(4-ethylpyridinium)methyl-7α-formamido-ceph-3-em-4-carboxylate 7β-[D-2-[2-Chloro-4,5-diacetoxyphenyl)-2-[(4-ethyl-2,3-dioxopiperazin-1-yl)carbonylamino]acetamido]-3-(4-ethylpyridinium)methyl-7α-formamido-ceph-3-em-4-carboxylate 7β-[D-2-[(4-Ethyl-2,3-dioxopiperazin-1-yl)carbonylamino]-2-phenylacetamido]-7α-formamido-3-(3-hydroxymethylpyridinium)methyl-ceph-3-em-4-carboxylate 7β-[D-2-[(4-Ethyl-2,3-dioxopiperazin-1-yl)carbonyl amino]-2-phenylacetamido]-7α-formamido-3-(4-methyl pyridinium)methyl-ceph-3-em-4-carboxylate 7β-[D-2-[(4-Ethyl-2,3-dioxopiperazin-1-yl)carbonyl amino]-2-phenylacetamido]-3-(3-ethyl-4-methyl pyridinium)methyl-7α-formamido-ceph-3-em-4-carboxylate 7β-[D-2-[(4-Ethyl-2,3-dioxopiperazin-1-yl)carbonyl amino]-2-phenylacetamido]-7α-formamido-3-[3-(3-hydroxypropyl)pyridinium]methyl-ceph-3-em-4-carboxylate 7β-[D-2-[(4-Ethyl-2,3-dioxopiperazin-1-yl)carbonyl amino]-2-phenylacetamido]-7α-formamido-3-(4-phenylpyridinium)methyl-ceph-3-em 4-carboxylate 3-(2,3-Cyclohexenopyridinium)methyl-7β-[D-2-([4-ethyl-2,3-dioxopiperazin-1-yl]carbonylamino)-2-phenylacetamido]-7α-formamido-ceph-3-em-4-carboxylate 7β-[D-2-[(4-Ethyl-2,3-dioxopiperazin-1-yl)carbonyl amino]-2-phenylacetamido]-7α-formamido-3-(3-methoxypyridinium)methyl-ceph-3-em-4-carboxylate 7β-[D-2-(3,4-Diacetoxyphenyl)-2-[(4-ethyl-2,3-dioxopiperazin-1-yl)carbonylamino]acetamido]-7α-formamido-3-(quinolinium)methyl-ceph-3-em-4-carboxylate 3-[4-(tert.-Butyl)pyridinium]methyl-7β-[D-2-[(4-ethyl-2,3-dioxopiperazin-1-yl)carbonylamino]-2-phenylacetamido]-7α-formamido-ceph-3-em-4-carboxylate 7β-[D-2-[(4-(3-Chlorophenyl)-2,3-dioxopiperazin-1-yl) carbonylamino]-2-phenylacetamido]-3-(4-ethylpyridinium) methyl-7α-formamido-ceph-3-em-4-carboxylate 7β-[D-2-[(4-Ethyl-2,3-dioxopiperazin-1-yl)carbonyl amino]-2-phenylacetamido]-7α-formamido-3-(4-methoxypyridinium)methyl-ceph-3-em-4-carboxylate 7β-[D-2-[(4-Ethyl-2,3-dioxopiperazin-1-yl)carbonyl amino]-2-phenylacetamido]-7α-formamido-3-[4-(prop-1-yl)pyridinium]methyl-ceph-3-em-4-carboxylate 7β-[D-2-[(4-Ethyl-2,3-dioxopiperazin-1-yl)carbonyl amino]-2-phenylacetamido]-3-(2-ethylpyridinium) methyl-7α-formamido-ceph-3-em-4-carboxylate 7β-[D-2-[(4-Ethyl-2,3-dioxopiperazin-1-yl)carbonyl amino]-2-phenylacetamido]-3-(3-ethylpyridinium) methyl-7α-formamido-ceph-3-em-4-carboxylate 3-(4-Cyclopropylpyridinium)methyl-7β-[D-2-[(4-ethyl-2,3-dioxopiperazin-1-yl)carbonylamino]-2-phenylacetamido]-7α-formamido-ceph-3-em-4-carboxylate 3-(4-Cyclopropylpyridinium)methyl-7β-[D-2-(3,4-diacetoxyphenyl)-2-[(4-ethyl-2,3-dioxopiperazin-1-yl) carbonylamino]acetamido]-7α-formamido-ceph-3-em-4-carboxylate 3-(4-Cyclopropylpyridinium)methyl-7β-[D-2-(3,4-dihydroxyphenyl)-2-[(4-ethyl-2,3-dioxopiperazin-1-yl) carbonylamino]acetamido]-7α-formamido-ceph-3-em-4-carboxylate 7β-[D-2-[(4-Ethyl-2,3-dioxopiperazin-1-yl) carbonylamino]-2-phenylacetamido]-7α-formamido-3-[4-(isopropyl)pyridinium]methyl-ceph-3-em-4-carboxylate 7β-[D-2-[(4-Ethyl-2,3-dioxopiperazin-1-yl)carbonyl amino]-2-phenylacetamido]-7α-formamido-3-[4-pyrid-2-yl)pyridinium]methyl-ceph-3-em-4-carboxylate 7β-[D-2-(3,4-Diacetoxyphenyl)-2-[(4-ethyl-2,3-dioxopiperazin-1-yl)carbonylamino]acetamido]-3-(4-ethyl pyridinium)methyl-7α-formamido-ceph-3-em-4-carboxylate 7β-[D-2-(3,4-Dihydroxyphenyl)-2-[(4-ethyl-2,3-dioxopiperazin-1-yl)carbonylamino]acetamido]-3-(4-ethyl pyridinium)methyl-7α-formamido-ceph-3-em-4-carboxylate The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a pharmaceutically acceptable compound of formula (Ia) or a pharmaceutically acceptable salt or pharmaceutically acceptable in vivo hydrolysable ester thereof together with a pharmaceutically acceptable carrier or excipient.

The compositions may be formulated for administration by any suitable route, such as oral or parenteral, or by topical application. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository base, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% to 99.5% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 mg to 12 g per day for an average adult patient (70 kg.), for instance 1500 mg per day, depending on the route and frequency of administration. Such dosages correspond to approximately 1.5 to 170 mg/kg per day. Suitably the dosage is from 1 to 6 g. per day.

The daily dosage is suitably given by administering a compound of the invention several times in a 24-hour period. Typically, 250 mg. is administered 4 times a day although, in practice, the dosage and frequency of administration which will be most suitable for an individual patient will vary with the age, weight and response of the patients, and there will be occasions when the physician will choose a higher or lower dosage and a different frequency of administration. Such dosage regimens are within the scope of this invention.

No toxicological effects are indicated when a pharmaceutically acceptable compound of the invention of formula (Ia) or a salt or in vivo hydrolysable ester thereof is administered in the above mentioned dosage range.

The antibiotic compounds according to the present invention may be the sole therapeutic agent in the compositions of the invention or a combination with other antibiotics and/or β-lactamase inhibitor may be employed.

Advantageously the compositions also comprise a compound of formula (III) or a pharmaceutically acceptable salt or ester thereof:

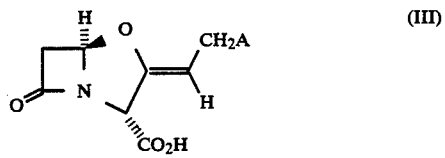

(III)

wherein A is hydroxyl; substituted hydroxyl; thiol; a group of formula $SO_2R^{13}$ wherein $R^{13}$ is $C_{1-6}$ alkyl; substituted thiol; amino; mono- or di-hydrocarbyl substituted amino; mono- or di-acylamino; an optionally substituted triazolyl group; or an optionally substituted tetrazolyl group as described in EP 0 053 893.

A further advantageous composition comprises a pharmaceutically acceptable antibiotic compound of the formula (Ia) or a salt or in vivo hydrolysable ester thereof and a pharmaceutically acceptable carrier or excipient together with a β-lactamase inhibitor of formula (IV) or a pharmaceutically acceptable salt or in vivo hydrolysable ester thereof:

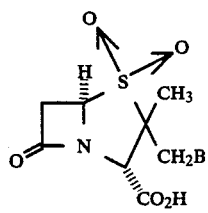

(IV)

wherein B is hydrogen, halogen or a group of formula:

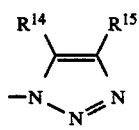

in which $R^{14}$ and $R^{15}$ are the same or different and each is hydrogen, $C_{1-6}$ alkoxycarbonyl, or carboxy or a pharmaceutically acceptable salt thereof.

Further suitable β-lactamase inhibitors include 6-alkylidene penems as described in European Patent Application No. 81301683.9 (Publication Number 0 041 768), and European Patent Application No. 85100521.5 (Publication Number 0 154 132) corresponding to laid open published Danish Patent Application No. 324/85.

Further suitable β-lactamase inhibitors include 6β-bromopenicillanic acid and salts and in vivo hydrolysable esters thereof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention of the formula (Ia) or a salt or in vivo hydrolysable ester thereof.

The pharmaceutically acceptable antibiotic compounds of the present invention of formula (Ia) or salts or in vivo hydrolysable esters thereof are active against a broad range of Gram positive and Gram negative bacteria, and may be used to treat a wide range of bacterial infections including those in immunocompromised patients.

Amongst many other uses, the pharmaceutically acceptable compounds of the invention of formula (Ia) or salts or in vivo hydrolysable esters thereof are of value in the treatment of respiratory tract and urinary tract infections in humans and may also be used to treat mastitis in cattle. A particular advantage of the antibacterially active compounds of this invention is their stability to β-lactamase enzymes and they are therefore effective against β-lactamase producing organisms.

The present invention further provides a process for the preparation of a compound of formula (I) which process comprises treating a compound of formula (V) or a salt thereof:

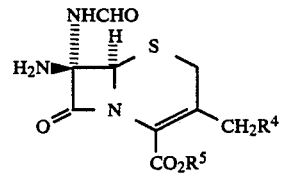

(V)

wherein $R^4$ and $R^5$ are as hereinbefore defined, wherein any reactive groups may be protected, and wherein the amino group is optionally substituted with a group which permits acylation to take place; with an N-acylating derivative of an acid of formula (VI):

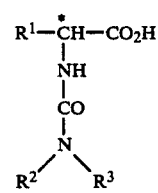

(VI)

wherein $R^1$, $R^2$, $R^3$ and * are defined with respect to formula (I) and wherein any reactive groups may be protected; and thereafter, if necessary or desired, carrying out one or more of the following steps:
(i) removing any protecting groups;
(ii) converting the group $-CO_2R^5$ into a different group $-CO_2R^5$;
(iii) converting the product into a salt.

The compounds of formula (Ia) may be prepared by a similar process, which process further comprises, if necessary, the step of converting the product into a pharmaceutically acceptable salt or a pharmaceutically acceptable in vivo hydrolysable ester.

It will be understood that in the compound of formula (V) the positive charge on $R^4$ is balanced by a counter anion which is either external or present on a group within the molecule.

Suitable groups which permit acylation to take place and which are optionally present on the amino group of the starting material of the formula (V) include N-silyl, N-stannyl and N-phosphorus groups, for example trialkylsilyl groups such as trimethylsilyl, trialkyltin groups such as tri-n-butyltin, groups of formula $-P.R^{16}R^{17}$ wherein $R^{16}$ is an alkyl, haloalkyl, aryl, aralkyl, alkoxy, haloalkyl, aryl, aralkyl, alkoxy, haloalkoxy, aryloxy, aralkyloxy or dialkylamino group, $R^{17}$ is the same as $R^{16}$ or is halogen or $R^{16}$ and $R^{17}$ together form a ring; suitable such phosphorus groups being $-P(OC_2H_5)_2$, $-P(C_2H_5)_2$,

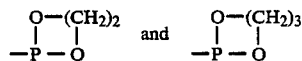

A preferred group for the above purpose is trimethylsilyl which may suitably be introduced in situ, prior to acylation, by causing an appropriate silylating reagent, e.g. trimethylsilyl chloride, to react with the compound of formula (V).

The silylation reaction may suitably be carried out in an inert anhydrous solvent, for example dichloromethane, in an inert atmosphere, preferably under argon. An organic base, for example N,N-dimethylaniline, may be added to facilitate the reaction. The reaction is normally carried out at an elevated temperature, suitably 30°-60° C.; preferably 40°-50° C.

A reactive N-acylating derivative of the acid (VI) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a ($C_{1-6}$)—1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (VI) or a salt or a reactive derivative thereof with a halogenating (eg chlorinating or brominating) agent such as phosphorus pentachloride, thionyl chloride, oxalyl chloride or phosgene.

Alternatively, the N-acylating derivative of the acid (VI) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid). When a symmetrical anhydride is employed, the reaction may be carried out in the presence of 2,6-lutidine as catalyst.

Alternative N-acylating derivatives of acid (VI) are the acid azide, or activated esters such as esters with 2-mercaptopyridine, cyanomethanol, p-nitrophenol,, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (VI) with an oxime.

Other reactive N-acylating derivatives of the acid (VI) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'-[3-(dimethylamino)propyl]-carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (VI) is to treat the acid of formula (VI) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (VI) so derived may then be caused to react with a compound of formula (V). The acylation reaction may conveniently be carried out at −40° to +30° C., if desired in the presence of an acid binding agent such as pyridine. A catalyst such as 4-dimethylaminopyridine may optionally also be added. A preferred solvent for the above acylation reaction is dichloromethane.

A preferred intermediate of formula (V) has the formula (VA):

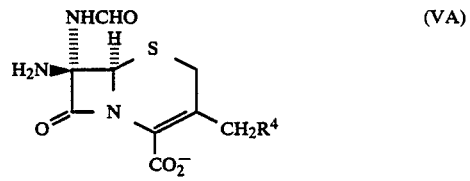

(VA)

wherein $R^4$ is as hereinbefore defined.

Accordingly, a preferred process for the preparation of a compound of formula (I) comprises treating a compound of formula (VA):

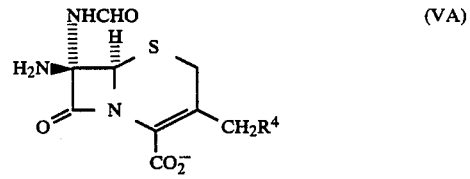

(VA)

wherein $R^4$ is hereinbefore defined, wherein any reactive groups may be protected, and wherein the amino group is optionally substituted with a group which permits acylation to take place; with an N-acylating derivative of an acid of formula (VI):

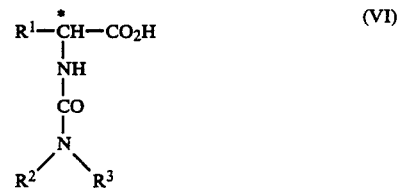

(VI)

wherein $R^1$, $R^2$, $R^3$ and * are defined with respect to formula (I) and wherein any reactive groups may be protected; and thereafter, if necessary or desired, carrying out one or more of the following steps:

(i) removing any protecting groups;
(ii) converting the group —$CO_2$— into a group —$CO_2R^5$;
(iii) converting the product into a salt.

The compounds of formula (Ia) may be prepared by a similar process, which process further comprises, if necessary, the step of converting the product into a pharmaceutically acceptable salt or a pharmaceutically acceptable in vivo hydrolysable ester.

A further preferred intermediate of formula (V) as hereinabove described has the formula (VII) or is an acid addition salt thereof:

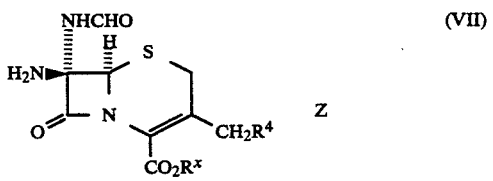

(VII)

wherein $R^4$ is defined with respect to formula (I); $R^x$ is hydrogen or a readily removable carboxy protecting group; and Z is an inorganic or organic anion present in the appropriate stoicheiometric proportion to balance the positive charge $R^4$.

Suitable readily removable carboxy protecting groups for $R^x$ include those listed hereinabove as suitable readily removable carboxy protecting groups for $R^5$.

The compounds of formula (I) may therefore also suitably be prepared by reacting a compound of formula (VII) as hereinabove defined or an acid addition salt thereof, wherein any reactive groups may be protected, with an N-acylating derivative of an acid of formula (VI) as hereinbefore defined (wherein any reactive groups may be protected); and thereafter, if necessary or desired, carrying out one or more of the following steps:

(i) removing any protecting groups;
(ii) converting the group $R^x$ into a group $R^5$;
(iii) converting the product into a salt.

For the compound of formula (VII) to react with an N-acylating derivative of an acid of formula (VI) it may first be necessary to introduce on to the amino group in the compound of formula (VII) a group which permits acylation to take place. Suitable such groups for this purpose include those listed hereinabove as being optionally present on the amino group in the compound of formula (V) prior to acylation.

A preferred group which may be introduced onto the amino group in the compound of formula (VII) is trimethylsilyl. Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis(-trimethylsilyl)acetamide, N,O-bis (trimethylsilyl)trifluoroacetamide, N-methyl-N-trimethylsilylacetamide, N-methyl-N-trimethylsilyltrifluoroacetamide, N,N'-bis(trimethylsilyl)urea, and N,O-bis(trimethylsilyl)carbamate. A preferred silylating agent is N-(trimethylsilyl)acetamide. The silylation reaction may suitably be carried out in an inert, anhydrous organic solvent such as dichloromethane at room temperature or at an elevated temperature, for example 30°-60° C., preferably 40°-50° C.

The above process may optionally be carried out in the presence of a small quantity, for example 0.1 equivalents, of a silyl halide, for example a tri($C_{1-6}$)alkylsilyl halide, especially trimethylsilyl chloride.

Preferred values of Z in compounds of formula (VII) are chloride and bromide.

As noted above, a reactive N-acylating derivative of the acid (VI) is employed in the preparation of a compound of formula (I) from a compound of formula (VII), the choice of reactive derivative being influenced by the chemical nature of the substituents of the acid of formula (VI).

Suitable N-acylating derivatives of the acid (VI) include those listed hereinbefore as suitable for use in the process for preparing a compound of formula (I) from a compound of formula (V). Methods for preparing such suitable N-acylating derivatives are as hereinabove described.

A preferred N-acylating derivative of the acid of formula (VI) is an acid halide, most preferably the acid chloride, which advantageously may be freshly prepared from the corresponding acid (VI) before use. Suitable halogenating agents for preparing acid halides from the acid of formula (VI) are hereinbefore described.

Preferred halogenating agents include oxalyl chloride, thionyl chloride, and phosgene.

In formula (VII) the group $CO_2R^x$ is preferably carboxy.

Other preferred groups for $R^x$ are diphenylmethyl (benzhydryl) and tri ($C_{1-6}$ alkyl)silyl, especially trimethylsilyl. The trimethylsilyl group may suitably be introduced onto the 4- carboxy group using silylating agents listed hereinabove as suitable for silylating the amino group in compounds of formula (VII).

The compounds of formula (V) herein which are, inter alia, intermediates for the compounds of formula (I) as hereinbefore defined may be prepared by reacting a compound of formula (VIII) or acid addition salt thereof:

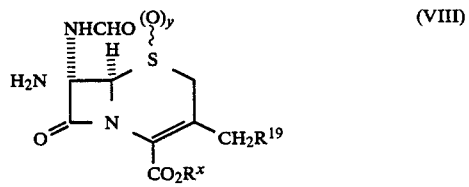

(VIII)

wherein $R^x$ is as hereinbefore defined, $R^{19}$ is a leaving group and y is 0 or 1; with a substituted pyridine of formula (IX), (X) or (XI):

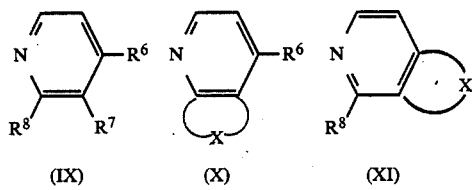

wherein $R^6$, $R^7$, $R^8$, and X are as hereinbefore defined; with the proviso that when $R^{19}$ is an acyloxy group, the group $CO_2R^x$ must be in the free acid form or a salt thereof; and thereafter if necessary:

(i) converting the group $R^x$ into a group $R^5$;
(ii) converting a sulphoxide (wherein y is 1) into a sulphide (wherein y is 0) by methods known in the art;
(iii) converting the product into a salt.

Suitable leaving groups $R^{19}$ include halide such as iodide or bromide or an acyloxy group such as, for example the acetoxy group.

Preferably R$^{19}$ is an acetoxy group or a bromine atom.

In the above process a particularly suitable acid addition salt of the starting material of the formula (VIII) is the trifluoroacetic acid salt.

Compounds of the formula (VIII) may be prepared as described in our co-pending European Patent Application No. 82303821.1 (Publication No. 0 071 395).

When R$^{19}$ is an acetoxy group, the conversion of compounds of formula (VIII) into compounds of formula (V) is preferably carried out in an aqueous medium, if necessary with a water-miscible organic solvent such as acetone present to give a homogeneous solution. The reaction may suitably be conducted in the presence of an alkali metal iodide, e.g. sodium iodide, or an alkali metal thiocyanate, e.g. potassium thiocyanate, and is generally carried out at an elevated temperature, for example between 40° and 80° C., and preferably at about 60° C.

When the reaction is complete (as adjudged, for example, by an analytical method such as reversed phase HPLC), the product may be isolated by chromatography on a suitable resin, for example 'Diaion HP 20SS' resin (obtained from Mitsubishi Chemical Corporation), and the product may thereafter, if necessary or desired, be modified to give a compound of formula (V) in which any reactive group which is present on R$^4$ may be protected.

Acid addition salts of the compound of formula (VII) as hereinbefore defined may suitably be prepared by reacting a compound of formula (VII) with a mineral acid.

In an alternative aspect, the acid addition salt of the compound of formula (VII) as hereinbefore defined may suitably be prepared by reacting a compound of formula (VA) with a mineral acid; and also, if necessary or desired, converting the carboxy group into a group CO$_2$R$^x$.

The above reactions may suitably be carried out in an aqueous medium at ambient temperature by addition of a dilute mineral acid, generally in the presence of a water-miscible organic solvent such as acetone, ethanol, propan-1-ol or propan-2-ol.

The reaction mixture may be chilled to 0°–10° C., generally to less than 5° C, to facilitate isolation of the product.

In a preferred aspect, the mineral acid used to convert a compound of the formula (VA) into an acid addition salt of a compound of formula (VII) has the formula HZ wherein Z is as defined with respect to formula (VII).

A particularly suitable mineral acid, for converting a compound of formula (VA) into an acid addition salt of a compound of formula (VII) is dilute hydrochloric acid.

Compounds of formula (V) and salts and protected derivatives thereof are novel and valuable intermediates; accordingly these compounds form another aspect of the present invention.

Specific compounds within formula (V) and salts thereof include the following compounds of formula (VA):

7β-Amino-3-(4-ethylpyridinium)methyl-7α-formamidoceph-3-em-4-carboxylate

7β-Amino-3-(2,3-cyclopentenopyridinium)methyl-7α-formamido-ceph-3-em-4-carboxylate 7β-Amino-7α-formamido-3-(3-hydroxymethylpyridinium) methyl-ceph-3-em-4-carboxylate 7β-Amino-7α-formamido-3-(4-methylpyridinium) methyl-ceph-3-em-4-carboxylate 7β-Amino-3-[4-(2-N-t-butoxycarbonylamino-2-carboxy)-ethylpyridinium]methyl-7α-formamido-ceph-3-em-4-carboxylate 7β-Amino-3-(3-ethyl-4-methylpyridinium)methyl-7α-formamido-ceph-3-em-4-carboxylate 7β-Amino-7α-formamido-3-[3-(3-hydroxypropyl) pyridinium]methyl-ceph-3-em-4-carboxylate 3-(3-Acetylpyridinium)methyl-7β-amino-7α-formamido-ceph-3-em-4-carboxylate 7β-Amino-7α-formamido-3-(4-phenylpyridinium)-methyl -ceph-3-em-4-carboxylate 7β-Amino-3-(3-carbamoylpyridinium)methyl-7α-formamido-ceph-3-em 4-carboxylate 7β-Amino-3-(2,3-cyclohexenopyridinium)methyl-7α-formamido-ceph-3-em-4-carboxylate 7β-Amino-7α-formamido-3-(3-methoxypyridinium)-methyl -ceph-3-em-4-carboxylate 7β-Amino-3-(3-chloropyridinium)methyl-7α-formamido-ceph-3-em-4-carboxylate 7β-Amino-7α-formamido-3-(quinolinium)methyl-ceph-3-em-4-carboxylate 7β-Amino-3-[4-(tert.-butyl)pyridinium]methyl-7α-formamido-ceph-3-em 4-carboxylate 7β-Amino-7α-formamido-3-(4-methoxypyridinium) methyl-ceph-3-em 4-carboxylate 7β-Amino-3-(4-carbamoylpyridinium)methyl-7α-formamido-ceph-3-em-4-carboxylate 7β-Amino-7α-formamido-3-[4-(prop-1-yl)pyridinium]-methyl-ceph-3-em-4-carboxylate 7β-Amino-7α-formamido-3-(isoquinolinium)methyl-ceph-3-em-4-carboxylate 7β-Amino-3-(2-ethylpyridinium)methyl-7α-formamido-ceph-3-em-4-carboxylate 7β-Amino-3-(3-ethylpyridinium)methyl-7α-formamido-ceph-3-em-4-carboxylate Sodium 7β-Amino-7α-formamido-3-[4-(2-sulfoethyl) pyridinium]methyl-ceph-3-em-4-carboxylate 7β-Amino-3-(4-cyclopropylpyridinium)methyl-7α-formamido-ceph-3-em-4-carboxylate 7β-Amino-7α-formamido-3-[4-(isopropyl) pyridinium]-methyl-ceph-3-em-4-carboxylate 7β-Amino-7α-formamido-3-[4-(pyrid-2-yl)pyridinium]-methyl-ceph-3-em-4-carboxylate Specific compounds within formula (V) and salts thereof include the following acid addition salt of the compound of formula (VII):

7β-Ammonio-3-(2,3-cyclopentenopyridinium)methyl-7α-formamido-ceph-3-em-4-carboxylic acid, dichloride salt The compounds of formula (I) may also suitably be prepared by reacting a compound of formula (XII):

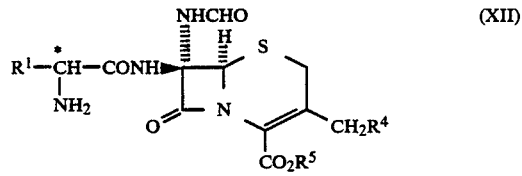

(XII)

wherein R$^1$, R$^4$, R$^5$ and * are as hereinbefore defined; the α-amino group is optionally substituted with a group which permits acylation to take place; and any reactive groups may be protected; with an N-acylating derivative of an acid of formula (XIII):

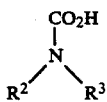 (XIII)

wherein any reactive groups may be protected; and thereafter, if necessary or desired, carrying out one or more of the following steps:
(i) removing any protecting groups;
(ii) converting the group —$CO_2R^5$ into a different group —$CO_2R^5$;
(iii) converting the product into a salt.

Compounds of formula (XII) above which are, inter alia, intermediates for the compounds of formula (I) may be prepared by reacting compounds of formula (V) as hereinbefore defined with an N-acylating derivative of an acid of formula (XIV):

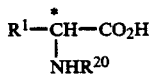 (XIV)

wherein $R^1$ and * are as hereinbefore defined and $R^{20}$ is an amino protecting group, and thereafter removing protecting group $R^{20}$.

Suitable amino-protecting groups $R^{20}$ are those well known in the art which may be removed under conventional conditions without disruption of the remainder of the molecule.

Examples of amino-protecting groups for $R^{20}$ include benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl optionally substituted by up to three halogen atoms, for example tert-butoxycarbonyl and 2,2,2-trichloroethoxycarbonyl; benzyloxycarbonyl optionally substituted as for benzyl above; allyloxycarbonyl; or trityl.

Compounds of formula (XII) may also be prepared by reacting a compound of formula (V) as hereinbefore defined with an N-acylating derivative of an α-azido acid of formula (XV):

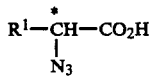 (XV)

wherein $R^1$ and * are as hereinbefore defined; followed by reduction of the azido group to an amino group by conventional methods, for example by catalytic hydrogenation or by reaction with triphenylphosphine followed by hydrolysis of the resultant phosphinimine.

Compounds of formula (XII) may also be prepared by reaction a compound of formula (V) as hereinbefore defined with an N-acylating derivative of an acid of formula (XVI):

 (XVI)

wherein $R^1$ and * are as hereinbefore defined; and hereinafter converting the phthalimido groups into an amino group by conventional methods.

The present invention further provides a process for the preparation of a compound of formula (I) which process comprises treating a compound of the formula (XVII)

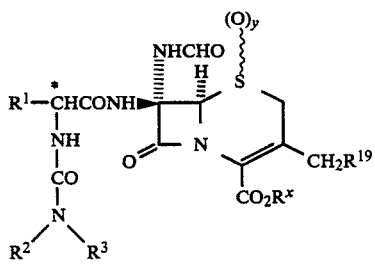 (XVII)

wherein $R^1$, $R^2$, $R^3$, $R^x$, $R^{19}$, y, and * are as hereinbefore defined; with a substituted pyridine of formula (IX), (X) or (XI) as hereinbefore defined; with the proviso that when $R^{19}$ is an acyloxy group, the group $CO_2R^x$ must be in the free acid form or a salt thereof; and thereafter if necessary:
(i) converting the group $R^x$ into a group $R^5$;
(ii) converting a sulphoxide (wherein y is 1) into a sulphide (wherein y is 0) by methods known in the art;
(iii) converting the product into a salt.

Suitable leaving groups $R^{19}$ include halide such as iodide or bromide or an acyloxy group such as, for example, the acetoxy group.

The present invention also provides a process for the preparation of a compound of formula (I) which process comprises treating a compound of the formula (XVIII):

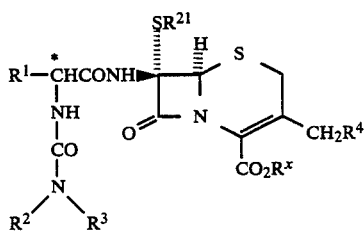 (XVIII)

wherein $R^1$, $R^2$, $R^3$, $R^4$ and * are as hereinbefore defined, and wherein any reactive groups may be protected, $R^x$ is hydrogen or a readily removable carboxy protecting group; and $R^{21}$ is $C_{1-6}$ alkyl, aryl or benzyl; with a heavy metal ion such as mercury, silver, thallium, lead or copper; and thereafter in situ with a nucleophilic derivative of formamide; and thereafter, if necessary, carrying out one or more of the following steps:
(i) removing any protecting groups;
(ii) converting the group $R^x$ into a group $R^5$;
(iii) converting the product into a salt;

The above process is analogous to that described in European Patent Application No. 84300338.5 (Publication Number 0 115 405).

At the end of the process described hereinabove and in other processes for the preparation of the compound of formula (I) described hereinbelow it may be necessary to remove protecting groups. Deprotection may be carried out by any convenient method known in the art that does not cause unwanted side reactions to occur to any appreciable extent. Methods that are particularly suitable for converting an acetoxy group in $R^1$ into a hydroxy group include treatment with aqueous sodium sulphite solution or aqueous sodium hydrogen carbonate solution, or treatment with an esterase, especially citrus acetylesterase. When a hydroxy group in $R^1$ is protected as a silyl ether, for example the trimethylsilyl ether, removal of the silyl group is normally carried out by acid hydrolysis.

In an alternative aspect, the present invention provides a process for the preparation of a compound of formula (I) which process comprises treating a compound of formula (XIX):

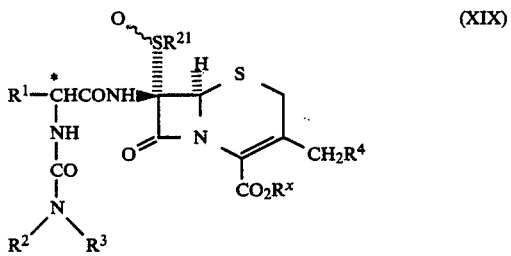

wherein $R^1$, $R^2$, $R^3$, $R^4$, *, $R^x$ and $R^{21}$ are as defined for formula (XVIII) and wherein any reactive groups may be protected; with a nucleophilic derivative of formamide; and thereafter, if necessary, carrying out one or more of the following steps.

(i) converting the group $R^x$ into a group $R^5$;
(ii) removing any protecting groups; and
(iii) converting the product into a salt.

The present invention further provides a process for the preparation of a compound of formula (I) which process comprises formylating a compound of formula (XX):

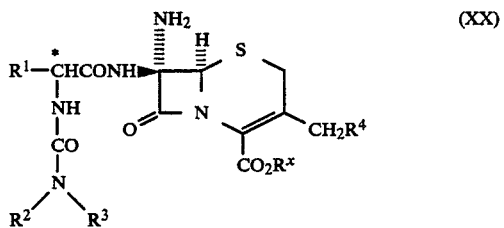

wherein $R^1$, $R^2$, $R^3$, $R^4$, $R^x$, and * are as hereinbefore defined and wherein any reactive groups may be protected; and thereafter, if necessary, carrying out one or more of the following steps.

(i) removing any protecting groups;
(ii) converting the group $R^x$ into a group $R^5$;
(iii) converting the product into a salt.

Suitable formylating agents include the reagent 4-formyl-2-methyl-1,3,4-thiadiazolin-5-thione (see H. Yazawa and S. Goto, Tetrahedron Letters, 1985, 26, 3703–3706), or mixed anhydrides such as formic acetic anhydride. The reaction may suitably be carried out in a temperature in the range −50° C. to 30° C. in aprotic solvent such as, for example, dichloromethane, chloroform, dimethylformamide, tetrahydrofuran, hexamethylphosphoramide, or dimethylsulphoxide, in the presence of a tertiary base. A preferred tertiary base employed in the reaction is a base of the pyridine type, such as pyridine, lutidine or picoline.

One process for preparing compounds within formula (XX) is disclosed in or is analogous to processes disclosed in European Patent Application No. 82303821.1 (Publication Number 0 071 395).

A further process for preparing compounds within formula (XX) comprises treating a compound of formula (XIX) with ammonia.

It will be apparent from the above that a process for preparing compounds of formula (I) comprises formamidylating a compound of formula (XXI):

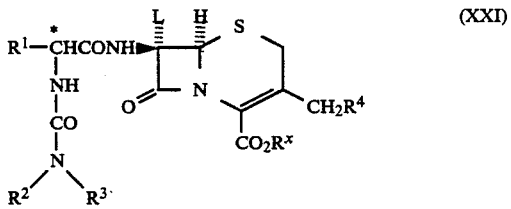

wherein L is $SR^{21}$, $SOR^{21}$ or $NH_2$; and $R^1$, $R^2$, $R^3$, $R^4$, $R^x$, $R^{21}$ and * are as hereinbefore defined.

As used herein the term 'formamidylating' denotes converting the group L into the group —NHCHO.

The antibiotic compounds of the present invention are active against a wide range of Gram-negative and Gram-positive organisms including E.coli such as, for example ESS, JT4, JT425 and NCTC 10418; Pseudomonas Spp. such as Ps.aeruginosa for example 10662 and Dalgleish; Serratia marcescens US32; Klebsiella aerogenes A; Enterobacter cloacae Nl; P.mirabilis such as, for example C977 and 889; P.morganii; P.rettgeri; B.subtilis; Staph aureus such as, for example Oxford and Russell; N.catarrhalis 1502; Strep faecalis I; β-Haemolytic Strep CN10.

The following Examples illustrate the preparation and biological activity of the compounds of the present invention.

Preparation 1

7β-Amino-7α-formamidocephalosporanic Acid t-Butyl 7β-amino-7α-formamidocephalosporanate (10 g, 27 mmol) was dissolved in trifluoroacetic acid (100 ml) at room temperature. After 1 h the solution was evaporated and the residue triturated with ether to give the title product as an off-white solid which was filtered off and dried in vacuo (7.95 g, 94%). This material was described previously, for example in Example 34(e) of European Patent Application No.0 071 395, as 7β-amino-7α-formamidocephalosporanic acid, trifluoroacetic acid salt.

EXAMPLE 1

7β-[D-2-[(4-Ethyl-2,3-dioxopiperazin-1-yl)carbonyl amino]-2-phenylacetamido]-3-(4-ethylpyridinium)methyl7α-formamido-ceph-3-em-4-carboxylate (a)

7β-Amino-3-(4-ethylpyridinium)methyl-7α-formamido-ceph-3-em-4-carboxylate

7β-Amino-7α-formamidocephalosporanic acid, (200 mg, 0.64 mmol) in water (8 ml) was treated with sodium iodide (670 mg, 4.47 mmol) and 4-ethylpyridine (428 mg, 4.0 mmol). Acetone was added, with stirring, to give an homogeneous solution. The mixture was heated to 60° C. and monitored by reverse phase HPLC for loss of starting material (reaction time approximately 6.5 h). After cooling to room temperature the mixture was concentrated at reduced pressure to remove the acetone. The concentrate was diluted with water and extracted with dichloromethane (x2). The aqueous phase was concentrated at reduced pressure. The concentrate was chromatographed on "Diaion HP20SS" resin (Mitsubishi Chemical Corp.), eluting initially with water, then with acetone/water mixtures. The product containing eluant was concentrated at reduced pressure, then lyophilised to give the title compound (100 mg); $v_{max}$ (KBr) 3368, 1767, 1675, 1635 (sh), and 1611 cm$^{-1}$; $\delta_H$ (D$_2$O) (major rotamer) 1.30 (3H, t, J 7.5 Hz), 2.96 (2H, q, J 7.5 Hz), 3.16 and 3.58 (together 2H, ABq, J 17.6 Hz), 5.24 and 5.35 (together 2H, ABq, J 14.7 Hz), 5.25 (1H, s), 7.92 (2H, d, J 6.4 Hz), 8.17 (1H, s), and 8.73 (2H, d, J 6.4 Hz); [F.A.B. (Thioglycerol) (+ve ion) MH+ 363].

(b) D-2-[(4-Ethyl-2,3-dioxopiperazin-1-yl)carbonyl amino]-2-phenylacetyl chloride To D-2-[(4-ethyl-2,3-dioxopiperazin-1-yl)carbonylamino]-2-phenylacetic acid (115 mg, 0.36 mmol) in dry dichloromethane (5 ml), containing a catalytic quantity of dry N,N-dimethylformamide, was added oxalyl chloride (91 mg, 0.72 mmol). The mixture was stirred at room temperature for 1.25 h, then evaporated at reduced pressure. The residue was taken up in dry dichloromethane and re-evaporated (x2). The residue was dried in vacuo and used without further purification; $v_{max}$ (CH$_2$Cl$_2$) 3280, 1800, 1720, and 1695 cm$^{-1}$.

(c) 7β-[D-2-[(4-Ethyl-2,3-dioxopiperazin-1-yl)carbonyl amino]-2-phenylacetamido]-3-(4-ethylpyridinium) methyl-7α-formamido-ceph-3-em-4-carboxylate 7β-Amino-3-(4-ethylpyridinium)methyl-7α-formamido-ceph-3-em-4-carboxylate (87 mg, 0.24 mmol) in dry dichloromethane (5 ml) containing N,N-dimethylaniline (233 mg, 1.92 mmol) and trimethylchlorosilane (104 mg, 0.96 mmol) was refluxed under argon for 45 min. The resulting solution was cooled and D-2-[(4-ethyl-2,3-dioxopiperazin-1-yl)carbonylamino]-2-phenylacetyl chloride (the product of example 1(b)) in dry dichloromethane (5 ml) added with stirring at room temperature. The reaction was monitored by reverse phase HPLC. After ca. 40 min the reaction was diluted with dichloromethane and extracted with water (x3). The combined aqueous extracts were washed with dichloromethane (x2). The aqueous phase was concentrated at reduced pressure and the concentrate chromatographed on HP20SS resin, eluting first with water, then acetone/water mixtures. The product containing eluant was concentrated at reduced pressure, then lyophilised to give the title compound (72 mg, containing approximately 20% of the L-isomer); $v_{max}$ (KBr) 3422, 3300 (sh), 1778, 1710 (sh), 1676, 1636, and 1616 cm$^{-1}$; $\delta_H$(D$_2$O) (D isomer, major rotamer) inter alia, 1.18 (3H, t, J 7.2 Hz), 1.32 (3H, t, J 7.6 Hz), 2.81 and 3.40 (together 2H, ABq, J 17.5 Hz), 2.97 (2H, q, J 7.6 Hz), 3.51 (2H, q, J 7.2 Hz), 3.66 (2H, m), 3.97 (2H, m), 5.14 and 5.31 (2H, ABq, J 14.4 Hz), 5.33 (1H, s), 5.49 (1H, s), 7.30–7.55 (5H, m), 7.89 (2H, d, J 6.1 Hz), 8.15 (1H, s), 8.67 (2H, d, J 6.1 Hz); [F.A.B. (Thioglycerol) (+ve ion) MH+ 664].

EXAMPLE 2

3-(2,3-Cyclopentenopyridinium)methyl-7β-[D-2-(3,4-di acetoxyphenyl)-2-[(4-ethyl-2,3-dioxopiperazin-1-yl) carbonylamino]acetamido]-7α-formamido-ceph-3-em-4-carboxylate

Method A (a)

7β-Amino-3-(2,3-cyclopentenopyridinium)methyl-7α-formamido-ceph-3-em-4-carboxylate To 7β-amino-7α-formamidocephalosporanic acid (0.6 g, 1.9 mmol) in water (10 ml) was added sodium iodide (2.0 g, 13.3 mmol) and 2,3- cyclopentenopyridine (1.43 g, 12.0 mmol). Acetone was added to give an homogeneous solution and the mixture was heated to 60° C., monitoring by reverse phase HPLC. After approximately 6 h the mixture was cooled to room temperature, and concentrated at reduced pressure. The concentrate was chromatographed on HP20SS resin, eluting first with water, then acetone/water mixtures. The product containing eluant was concentrated at reduced pressure, then lyophilised to give the title compound (0.35 g); $v_{max}$ (KBr) 3402, 3275 (sh), 1768, 1675, and 1616 cm$^{-1}$; $\delta_H$ (D$_2$O) (major rotamer) 2.20–2.40 (2H, m), 3.05–3.25 (3H, m), 3.25–3.45 (2H, m), 3.50 (1H,lower field arm of ABq, J 17.6 Hz), 5.22 and 5.36 (together 2H, ABq, J 15.2 Hz), 5.23 (1H, s), 7.76 (1H, m), 8.16 (1H, s), 8.28 (1H, d, J 7.7 Hz), 8.49 (1H, d, J 6.2 Hz); [F.A.B. (+ve ion) (Thioglycerol) MH+ 375].

(b) D-2-(3,4-Diacetoxyphenyl)-2-[(4-ethyl-2,3-dioxo piperazin-1-yl)carbonylamino]acetyl chloride To D-2-(3,4-diacetoxyphenyl)-2-[(4-ethyl-2,3-dioxopiperazin-1-yl)carbonylamino]acetic acid (786 mg, 1.77 mmol) in dry dichloromethane (15 ml), containing a catalytic quantity of dry N,N-dimethylformamide, at 0° C. was added oxalyl chloride (448 mg, 3.53 mmol). The mixture was stirred and allowed to warm to room temperature. After 1.25 h the mixture was evaporated at reduced pressure. The residue was taken up in dry dichloromethane and re-evaporated (x2). The residue was dried in vacuo and used directly without further purification; $v_{max}$ (CH$_2$Cl$_2$) 3275, 1790 (sh), 1775, 1715, and 1690 cm$^{-1}$.

(c)

3-(2,3-Cyclopentenopyridinium)methyl-7β-[D-2-(3,4-diacetoxyphenyl)-2-[(4-ethyl-2,3-dioxopiperazin-1-yl)carbonylamino]acetamido]-7α-formamido-ceph-3-em-4-carboxylate 7β-Amino-3-[(2,3-cyclopentenopyridinium)methyl]-7α-formamido-ceph-3-em 4-carboxylate (330 mg, 0.88 mmol) in dry dichloromethane (15 ml) containing N,N-dimethylaniline (853 mg, 7.04 mmol) and trimethylchlorosilane (573 mg, 5.28 mmol) was refluxed under argon for 30 min. The resulting solution was cooled and a solution of D-2-(3,4-diacetoxyphenyl)-2-[(4-ethyl-2,3-dioxopiperazin-1-yl)carbonylamino]acetyl chloride (3/5th of the product of example 2(b)) in dry dichloromethane (6 ml) added with stirring at room temperature.

The reaction was monitored by reverse phase HPLC. When reaction was complete, the mixture was diluted with dichloromethane and extracted with water (x3). The combined aqueous extracts were washed with dichloromethane (x2). The aqueous phase was concentrated at reduced pressure and the concentrate chromatographed on HP20SS resin, eluting initially with water, then acetone/water mixtures. The product containing eluant was concentrated at reduced pressure, then lyophilised to give the title compound (395 mg, containing ca. 30% of the L isomer); $\nu_{max}$ (KBr) 3390 (sh), 3289, 1772, 1710 (sh), 1682, and 1617 cm$^{-1}$; $\delta_H$ (D$_2$O) (D isomer, major rotamer) inter alia 1.17 (3H, t, J 7.2 Hz), 2.10–2.40 (8H, m), 2.69 (1H, upper field arm of ABq, J 17.3 Hz), 3.05–3.40 (5H, m), 3.49 (2H, q, J 7.2 Hz), 3.55–3.75 (2H, m), 3.80–4.10 (2H, m), 5.15–5.40 (2H, m), 5.32 (1H, s), 5.50 (1H, s), 7.20–7.55 (3H, m), 7.65–7.80 (1H, m), 8.15 (1H, s), 8.20–8.50 (2H, m); [F.A.B. (+ve ion) (CHCl$_3$/diamylphenol) MH+ 792].

Method B (d)

7β-Ammonio-3-(2,3-cyclopentenopyridinium)methyl-7α-formamido-ceph-3-em-4-carboxylic acid, dichloride salt 7β-Amino-3-(2,3-cyclopentenopyridinium)methyl-7α-formamido-ceph-3-em-4-carboxylate (130 mg; 0.35 mmol), in 2.5N hydrochloric acid (0.5 ml) was added to vigorously stirred propan-2-ol (50 ml), rinsing in any remaining material with more 2.5N hydrochloric acid (2×0.25 ml). The resulting suspension was stored at ca. 0° C. for 1 h. The solid was filtered off, washed with propan-2-ol and dried in vacuo over phosphorus pentoxide, giving the title compound (79 mg, 51%); $\lambda_{max}$ (H$_2$O) 270 nm (em 9860); $\nu_{max}$ (KBr) 3362, 2560 (sh), 1980 (wk), 1789, 1687, and 1618 cm$^{-1}$; $\delta_H$(D$_2$O) (major rotamer) 2.30 (2H, apparent quintet, J 7.7 Hz), 3.17 (2H, t, J 7.7 Hz), 3.31 and 3.55 (2H, Abq, J 17.8 Hz), 3.33 (2H, t, J 7.6 Hz), 5.31 (1H, s), 5.35 and 5.45 (2H, ABq, J 15.3 Hz), 7.65–7.85 (1H, m), 8.26 (1H, s, obscuring 1H, d, J 8.3 Hz), 8.40–8.60 (1H, m); [FAB (+ve ion) (thioglycerol) MH+ (free base) 375].

(e)

3-(2,3-Cyclopentenopyridinium)methyl-7β-[D-2-(3,4-diacetoxyphenyl)-2-[(4-ethyl-2,3-dioxopiperazin-1-yl)carbonylamino]acetamido]-7α-formamido-ceph-3-em-4-carboxylate A suspension of 7β-ammonio-3-(2,3-cyclopentenopyridinium)methyl-7α-formamido-ceph-3-em 4-carboxylic acid, dichloride salt, (69 mg; 0.154 mmol) in dry dichloromethane (5 ml) containing N-(trimethylsilyl) acetamide (224 mg; 1.54 mmol) was stirred at room temperature for 3.75 h, when complete dissolution had occurred. A solution of D-2-(3,4-diacetoxyphenyl)-2-[(4-ethyl-2,3-dioxopiperazin-1-yl)carbonylamino]acetyl chloride (freshly prepared from the corresponding acid (101 mg; 0.231 mmol) via the method described in Example 2(b)) in dry dichloromethane (3 ml) was added (reverse phase h.p.l.c. monitoring). After 0.33 h, a further portion of D-2-(3,4-diacetoxyphenyl)-2-[(4-ethyl-2,3-dioxopiperazin-1-yl)carbonylamino]acetyl chloride (0.077 mmol) in dry dichloromethane (1 ml) was added, and after a further 1 h purification as in Example 2(c) afforded the title compound (37 mg, 28%).

EXAMPLE 3

3-(2,3-Cyclopentenopyridinium)methyl-7β-[D-2-(3,4-dihydroxyphenyl)-2-[(4-ethyl-2,3-dioxopiperazin-1-yl)carbonylamino]acetamido]-7α-formamido-ceph-3-em-4-carboxylate To a stirred solution of 3-(2,3-cyclopentenopyridinium)methyl-7β-[D-2-(3,4-diacetoxyphenyl)-2-[(4-ethyl-2,3-dioxopiperazin-1-yl)carbonylamino]acetamido]-7α-formamido-ceph-3-em 4-carboxylate (354 mg, 0.45 mmol) in water (20 ml) at room temperature was added 2.5% (w/v) aqueous sodium carbonate solution to pH 8.0, followed by sodium sulphite (142 mg, 1.13 mmol) in one portion. The pH of the mixture was maintained at 8.5/9.0 by the addition of more 2.5% (w/v) aqueous sodium carbonate solution. The reaction was monitored by reverse phase HPLC. After ca. 40 min, the crude mixture was chromatographed on HP20SS, eluting initially with water then acetone/water mixtures. The product containing eluant was concentrated at reduced pressure and the concentrate lyophilised to give the title compound (213 mg, containing ca. 25% of the L isomer); $\lambda_{max}$ (H$_2$O) 271 nm ($\epsilon_m$ 17034); $\nu_{max}$ (KBr) 3400, 3299, 1779, 1710 (sh), 1676, and 1616 cm$^{-1}$; $\delta_H$(D$_2$O) (D isomer, major rotamer) inter alia 1.17 (3H, t, J 7.2 Hz), 2.0–2.4 (2H, m), 2.80 (1H, higher field arm of ABq, J 17.5 Hz), 3.10–3.75 (9H, complex m), 3.80–4.10 (2H, m), 5.1–5.4 (4H, m), 6.70–7.00 (3H, m), 7.65–7.80 (1H, m), 8.14 (1H, s), 8.15–8.50 (2H, m); [F.A.B. (+ve ion) (Thioglycerol) MH+ 708].

EXAMPLE 4

7β-[D,L-2-[(4-Ethyl-2,3-dioxopiperazin-1-yl)carbonyl amino]-2-(fur-2-yl)acetamido]-7α-formamido-3-(4-ethyl pyridinium)methyl-ceph-3-em-4-carboxylate 7β-Amino-3-(4-ethylpyridinium)methyl-7α-formamido-ceph-3-em-4-carboxylate (75 mg, 0.208 mmol) in dry dichloromethane (7 ml) containing N,N-dimethylaniline (202 mg, 1.66 mmol) and trimethylchorosilane (136 mg, 1.25 mmol) was refluxed under argon for ca. 0.5 h. The resulting solution was cooled and a solution of D,L-2-[(4-ethyl-2,3-dioxopiperazin-1-yl)carbonylamino]-2-(fur-2-yl) acetyl chloride (freshly prepared from the corresponding acid (80 mg; 0.26 mmol) via the method described in Example 1(b)) in dry dichloromethane (5 ml) added with stirring at room temperature. The reaction was monitored by reverse phase HPLC. After 2 h, purification as described in Example 1(c) afforded the title compound (43 mg; 32%); $\gamma_{max}$ (KBr) 3417, 3300 (sh), 1775, 1710 (sh), 1675, 1640, and 1615 cm$^{-1}$; $\delta_H$(D$_2$O) (D/L ratio ca. 3:2) (major rotamers) 1.20 (3H, t, J 7.2 Hz), 1.33 (3H, t, J 7.5 Hz), 2.98 (2H, q, J 7.5 Hz, obscuring 1H, higher field arm of ABq), 3.40–3.63 (3H, m), 3.65–3.80 (2H, m), 3.90–4.15 (2H, m), 5.15–5.55 (3H, m), 5.70 (0.6H, s), 5.72 (0.4H, s), 6.35–6.70 (2H, m), 7.45–7.65 (1H, m), 7.80–8.00 (2H, m), 8.17 (0.4H, s), 8.18 (0.6H, s), and 8.60–8.80 (2H, m); [F.A.B. (+ve ion) (Glycerol/H$_2$O) MH+ 654].

EXAMPLE 5 7β-[D,L-2-[(4-Ethyl-2,3-dioxopiperazin 1-yl)carbonyl amino]-2-(thien-2-yl)acetamido]-3-(4-ethylpyridinium) methyl-7α-formamido-ceph-3-em-4-carboxylate 7β-Amino-3-(4-ethylpyridinium)methyl-7α-formamido-ceph-3-em 4-carboxylate (181 mg, 0.50 mmol) in dry dichloromethane (7 ml) containing N,N-dimethylaniline (485 mg, 4.0 mmol) and trimethylchlorosilane (362 mg, 3.0 mmol) was refluxed under argon for ca. 0.5 h. The resulting solution was cooled and a solution of D,L-2-[(4-ethyl-2,3-dioxopiperazin-1-yl)carbonylamino]-2-(thien-2-yl) acetyl chloride (freshly prepared from the corresponding acid (244 mg, 0.75 mmol) via the method described in Example 1(b)) in dry dichloromethane (5 ml) added with stirring at room temperature. The reaction was monitored by reverse phase HPLC. After ca. 0.25 h, purification as described in Example 1(c) afforded the title compound (160 mg, 48%); $\lambda_{max}$ (H$_2$O) 227 nm ($\epsilon_m$ 24218); $\nu_{max}$ (KBr) 3380, 3280, 1781, 1710 (sh), 1684, 1635, and 1615 cm$^{-1}$; $\delta_H$ (D$_2$O) (D/L ratio ca. 3:2) (major rotamers) 1.18 (3H, t, J 7.2 Hz), 1.30 (3H, t, J 7.5 Hz), 2.96 (2H, q, J 7.5 Hz, obscuring 1H, higher field arm of ABq), 3.50 (2H, q, J 7.2 Hz, obscuring 1H, lower field arm of ABq), 3.60–3.80 (2H, m), 3.90–4.10 (2H, m), 5.18 and 5.33 (together 1.2H, ABq, J 14.5 Hz), 5.21 and 5.41 (together 0.8H, ABq, J 14.5 Hz), 5.29 (0.4H, s), 5.35 (0.6H, s), 5.80 (0.6H, s), 5.82 (0.4H, s), 6.95–7.10 (1H, m), 7.15–7.30 (1H, m), 7.32–7.50 (1H, m), 7.80–8.00 (2H, m), 8.13 (0.4H, s), 8.16 (0.6H, s), and 8.55–8.80 (2H, m); [F.A.B. (+ve ion) (Thioglycerol/MeOH) MH+ 670].

EXAMPLE 6

7β-[D,L-2-[(4-Ethyl-2,3-dioxopiperazin-1-yl)carbonyl amino]-2-(3,4-methylenedioxyphenyl)acetamido]-3-(4-ethylpyridinium)methyl-7α-formamido-ceph-3-em-4-carboxylate 7β-Amino-3-(4-ethylpyridinium)methyl-7α-formamido-ceph-3-em-4-carboxylate (91 mg; 0.25 mmol) in dry dichloro methane (10 ml) containing N,N-dimethylaniline (243 mg, 2.0 mmol) and trimethylchlorosilane (163 mg, 1.5 mmol) was refluxed under argon for ca. 0.5 h. The resulting solution was cooled and a solution of D,L-2-[(4-ethyl-2,3-dioxopiperazin-1-yl)carbonylamino]-2-(3,4methylenedioxyphenyl)acetyl chloride (freshly prepared from the corresponding acid (113 mg, 0.31 mmol) via the method described in Example 1(b)) in dry dichloromethane (5 ml) added with stirring at room temperature. The reaction was monitored by reverse phase HPLC. After ca. 0.75 h, purification as described in Example 1(c) afforded the title compound (74 mg; 42%); $\lambda_{max}$ (H$_2$O) 249 nm ($\epsilon_m$ 18991); $\nu_{max}$ (KBr) 3410, 3300 (sh), 1779, 1710 (sh), 1676, 1640, and 1616 cm$^{-1}$; $\delta_H$(D$_2$O) (D/L ratio ca. 4:1) (major rotamers) 1.19 (3H, t, J 7.2 Hz), 1.32 (3H, t, J 7.5 Hz), 2.80–3.10 (3H, m), 3.35–3.60 (3H, m), 3.60–3.80 (2H, m), 3.85–4.10 (2H, m), 5.10–5.50 (4H, m), 5.75–6.05 (2H, m), 6.75–7.10 (3H, m), 7.80–8.00 (2H, m), 8.13 (0.2H, s), 8.16 (0.8H, s), and 8.65–8.80 (2H, m); [F.A.B. (+ve ion) (Thioglycerol) MH+ 708].

EXAMPLE 7

7β-[D-2-[2-Chloro-4,5-diacetoxyphenyl)-2-[(4-ethyl-2,3-dioxopiperazin-1-yl)carbonylamino]acetamido]-3-(4-ethylpyridinium)methyl-7α-formamido-ceph-3-em-4-carboxylate 7β-Amino-3-(4-ethylpyridinium)methyl-7α-formamido-ceph-3-em-4-carboxylate (91 mg, 0.25 mmol) in dry dichloromethane (7 ml) containing N,N-dimethylaniline (243 mg, 2.0 mmol) and trimethylchlorosilane (163 mg, 1.5 mmol) was refluxed under argon for ca. 0.5 h. The resulting solution was cooled and a solution of D-2-[(4-ethyl-2,3-dioxopiperazin-1-yl)carbonylamino]-2-(2-chloro-4,5-diacetoxyphenyl)acetyl chloride (freshly prepared from the corresponding acid (147 mg, 0.313 mmol) via the method in Example 2(b)) in dry dichloromethane (5 ml) was added with stirring at room temperature. The reaction was monitored by reverse phase HPLC. After ca. 0.75 h, purification as described in Example 1(c) gave the title compound (60 mg; 28%); $\nu_{max}$(KBr) 3400, 3290, 1776, 1710 (sh), 1684, 1640, and 1620 cm$^{-1}$; $\delta_H$ (D$_2$O) (D isomer; major rotamer) inter alia 1.21 (3H, t, J 7.0 Hz), 1.35 (3H, t, J 7.5 Hz), 2.20–2.45 (6H, m), 2.80–3.10 (3H, m), 3.40–3.63 (3H, m), 3.64–3.85 (2H, m), 3.85–4.15 (2H, m), 5.10–5.70 (3H, m), 5.97 (1H, s), 7.30–7.60 (2H, m), 7.80–8.05 (2H, m), 8.20 (1H, s), and 8.55–8.85 (2H, m); [F.A.B. (+ve ion) (Thioglycerol) MH+ 814].

EXAMPLE 8

7β-[D-2-[(4-Ethyl-2,3-dioxopiperazin-1-yl)carbonyl amino]-2-phenylacetamido]-7α-formamido-3-(3-hydroxy methylpyridinium)methyl-ceph-3-em-4-carboxylate (a) 7β-Amino-7α-formamido-3-(3-hydroxymethyl pyridinium)methyl-ceph-3-em-4-carboxylate 7β-Amino-7α-formamidocephalosporanic acid (0.2 g; 0.64 mmol) in water (6 ml) was reacted with sodium iodide (0.846 g; 5.64 mmol) and 3-pyridinemethanol (0.271 ml; 2.82 mmol) as described in Example 2(a) to give the title compound (0.098 g; 43%); $\nu_{max}$ (KBr) 3372, 1764, 1670, and 1611 cm$^{-1}$; $\delta_H$ (D$_2$O) (major rotamer) 3.19 and 3.63 (2H, ABq, J 17.6 Hz), 4.91 (2H, s), 5.28 (1H, s), 5.35 and 5.48 (2H, ABq, J 14.7 Hz), 8.11 (1H, dd, J 7.7 and 5.9 Hz), 8.19 (1H, s), 8.56 (1H, d, J 7.7 Hz), 8.87 (1H, d, J 5.9 Hz), and 8.95 (1H, s).

(b) 7β-[D-2-[(4-Ethyl-2,3-dioxopiperazin-1-yl) carbonylamino]-2-phenylacetamido]-7α-formamido 3-(3-hydroxymethylpyridinium)methyl-ceph-3-em-4-carboxylate 7β-Amino-7α-formamido-3-(3-hydroxymethylpyridinium) methyl-ceph-3-em-4-carboxylate (75 mg; 0.21 mmol) was suspended in anhydrous dichloromethane (5 ml), chlorotrimethylsilane (0.14 ml; 1.26 mmol) and N,N-dimethylaniline (0.27 ml; 2.13 mmol) added under argon and the mixture refluxed for 1h. The resulting solution was cooled to room temperature and D-2-[(4-ethyl-2,3-dioxopiperazin-1-yl)carbonylamino]-2-phenylacetyl chloride (prepared from the corresponding acid (88 mg; 0.28 mmol) as described in Example 1(b)) in anhydrous dichloromethane (0.5 ml) added. After a further 0.5 h purification as described in Example 1(c), afforded the title compound (50 mg; 36%); $\lambda_{max}$ (H$_2$O) 256 nm ($\epsilon_m$ 14152); $\nu_{max}$ (KBr) 3291, 1782, 1715, 1675, and 1615 cm$^{-1}$; $\delta_H$(D$_2$O) (D isomer; major rotamer) inter alia 1.17 (3H, t, J 7.2 Hz), 2.86 (1H, d, J 17.6 Hz; higher field arm of ABq), 3.47 (2H, q, J 7.2 Hz; lower field arm of ABq; overlaps 1H, d), 3.65 (2H, m), 3.95 (2H, m), 4.84 (2H, s), 5.1–5.6 (4H, complex m), 7.3–7.6 (5H, m), 8.0–8.2 (2H, m), 8.51 (1H, m), and 8.7–8.95 (2H, m); [F.A.B. (Thioglycerol/H$_2$O) MH+ 666].

EXAMPLE 9

7β-[D-2-[(4-Ethyl-2,3-dioxopiperazin-1-yl)carbonyl amino]-2-phenylacetamido]-7α-formamido-3-(4-methyl pyridinium)methyl-ceph-3-em-4-carboxylate (a) 7β-Amino-7α-formamido-3-(4-methylpyridinium) methyl-ceph-3-em 4-carboxylate 7β-Amino-7α-formamidocephalosporanic acid (0.2 g; 0.64 mmol) was reacted with sodium iodide (0.846 g; 5.64 mmol) and 4-methylpyridine (0.274 ml; 2.82 mmol) in water (6 ml) as described in Example 2(a) to afford the title compound (0.091 g; 41%); $\nu_{max}$ (KBr) 3371, 1762, 1675, 1640, and 1611 cm$^{-1}$; $\delta_H$ (D$_2$O) (major rotamer) 2.64 (3H, s), 3.15 and 3.58 (2H, ABq, J 17.6 Hz), 5.23 and 5.34 (2H, ABq, J 14.7 Hz), 5.26 (1H, s), 7.88 (2H, d, J 6.3 Hz), 8.16 (1H, s), and 8.69 (2H, d, J 6.5 Hz).

(b) 7β-[D-2-[(4-Ethyl-2,3-dioxopiperazin-1-yl)carbonyl amino]-2-phenylacetamido]-7α-formamido-3-(4-methyl pyridinium)methyl-ceph-3-em-4-carboxylate 7β-Amino-7α-formamido-3-(4-methylpyridinium)methyl-ceph -3-em 4-carboxylate (86 mg; 0.247 mmol) was acylated as described in Example 8 to afford the title compound (62 mg; 39%) containing ca. 20% L-isomer; $\lambda_{max}$ (H₂O) 253 nm ($\epsilon_m$ 15783); $\nu_{max}$ (KBr) 3400, 1780, 1710, 1680, 1636, and 1610 cm⁻¹; $\delta_H$ (D₂O) (D-isomer; major rotamer) inter alia 1.18 (3H, t, J 7.2 Hz), 2.66 (3H, s), 2.83 and 3.42 (2H, ABq, J 17.6 Hz), 3.50 (2H, m), 3.70 (2H, m), 4.0 (2H, m), 5.1–5.5 (4H, complex m), 7.3–7.6 (5H, m), 7.86 (2H, broadened d, J 5.9 Hz), 8.15 (1H, s), and 8.63 (2H, d, J 6.6 Hz); [F.A.B. (Glycerol/ H₂O) MH+ 650].

EXAMPLE 10

7β-Amino-3-[4-(2-N-t-butoxycarbonylamino-2-carboxy) ethylpyridinium]methyl-7α-formamido -ceph-3-em-4-carboxylate 7β-Amino-7α-formamidocephalosporanic acid (100 mg; 0.317 mmol) was dissolved in water (12 ml) and acetone (1 ml) containing sodium iodide (418 mg; 2.78 mmol) and 4-[2-N-t-butoxycarbonylamino-2-carboxy]ethylpyridine (403 mg; 1.39 mmol). The mixture was heated at 60° C. for 6 h, cooled, filtered and the filtrate concentrated. The concentrate was purified as described in Example 2(a) to afford the title compound (143 mg) containing ca. 20% 4-(2-N-t-butoxycarbonylamino-2-carboxy) ethylpyridine; $\nu_{max}$ (KBr) 3403, 1764, 1683, and 1608 cm⁻¹; $\delta_H$ (D₂O) (major rotamer) inter alia 1.34 (9H, s), 3.0–3.3 (2H, m), 3.4–3.7 (2H, m), 4.42 (1H, m), 5.25 (1H, s), 5.28 and 5.40 (2H, ABq, J 14.6 Hz), 7.96 (2H, d, J 6.5 Hz), 8.16 (1H, s), and 8.81 (2H, d, J 6.5 Hz); [F.A.B. (Thioglycerol) MH+ 522].

EXAMPLE 11

7β-[D-2-[(4-Ethyl-2,3-dioxopiperazin-1-yl)carbonyl amino]-2-phenylacetamido]-3-(3-ethyl-4-methyl pyridinium)methyl-7α-formamido-ceph-3-em 4-carboxylate (a) 7β-Amino 3-(3-ethyl-4-methylpyridinium)methyl-7α-formamido-ceph-3-em-4-carboxylate 7β-Amino-7α-formamidocephalosporanic acid (0.2 g; 0.64 mmol) was dissolved in water (6 ml) containing sodium iodide (0.846 g; 5.64 mmol) and 3-ethyl-4-methylpyridine (0.341 g; 2.82 mmol) and the mixture heated at 60° C. for 7 h. The solution was cooled, concentrated to ca. 2 ml in vacuo and the title product (0.098 g; 41%) isolated as described in Example 2(a); $\nu_{max}$ (KBr) 3367, 3300, 1767, 1676, and 1616 cm⁻¹; $\delta_H$ (D₂O) (major rotamer) 1.25 (3H, t, J 7.5 Hz), 2.57 (3H, s), 2.81 (2H, q, J 7.5 Hz), 3.11 and 3.53 (2H, ABq, J 17.5 Hz), 5.18 and 5.29 (2H, ABq, J 14.7 Hz), 5.22 (1H, s), 7.79 (1H, d, J 6 Hz), 8.14 (1H, s), 8.53 (1H, d, J 6 Hz), and 8.58 (1H, s); [F.A.B. (Glycerol/H₂O) MH+ 377].

(b) 7β-[D-2-[(4-Ethyl-2,3-dioxopiperazin-1-yl)carbonyl amino]-2-phenylacetamido]-3-(3-ethyl-4-methyl pyridinium)methyl-7α-formamido-ceph-3-em-4-carboxylate 7β-Amino-3-(3-ethyl-4-methylpyridinium)methyl-7α-formamido-ceph-3-em-4-carboxylate (98 mg; 0.26 mmol) was suspended in anhydrous dichloromethane (5 ml) containing chlorotrimethylsilane (0.2 ml; 1.56 mmol) and N,N-dimethylaniline (0.25 ml; 2.08 mmol) and the mixture refluxed for 1h. The resulting solution was cooled to room temperature and a solution of D-2-[(4-ethyl-2,3-dioxopiperazin-1-yl)carbonylamino]-2-phenylacetyl chloride (prepared from the corresponding acid (125 mg; 0.39 mmol) as described in Example 1(b)) in anhydrous dichloromethane (0.5 ml) added. After a further 1h, the title product (35 mg; 19%) (containing ca. 25% of the L isomer) was isolated as described in Example 1(c); $\lambda_{max}$ (H₂O) 257 nm ($\epsilon_m$ 16714); $\nu_{max}$ (KBr) 3400, 3300, 1780, 1710, 1682, and 1617 cm⁻¹; $\delta_H$ (D₂O) (D isomer; major rotamer) inter alia 1.15 (3H, t, J 7.1 Hz), 1.21 (3H, t, J 7.5 Hz), 2.56 (3H, s), 2.7–2.9 (3H, m), 3.3–3.55 (3H, m), 3.64 (2H, broad s), 3.94 (2H, m), 5.07 and 5.25 (2H, ABq, J 14.6 Hz), 5.31 (1H, s), 5.46 (1H, s), 7.2–7.5 (5H, m), 7.76 (1H, d, J 6 Hz), 8.13 (1H, s), 8.46 (1H, d, J 6 Hz), and 8.53 (1H, s); [F.A.B. (Glycerol/H₂O) MH+ 678].

EXAMPLE 12

7β-[D-2-[(4-Ethyl-2,3-dioxopiperazin-1-yl)carbonyl amino]-2-phenylacetamido]-7α-formamido-3-[3-(3-hydroxy propyl)pyridinium]methyl-ceph-3-em-4-carboxylate (a) 7β-Amino-7α-formamido-3-[3-(3-hydroxypropyl) pyridinium]methyl-ceph-3-em-4-carboxylate 7β-Amino-7α-formamidocephalosporanic acid (0.3 g; 0.95 mmol) was reacted with sodium iodide (1.26 g; 8.4 mmol) and 3-(3-pyridyl)propan -1-ol (0.55 ml; 4.2 mmol) in water as described in Example 2(a) to give the title compound (0.167 g; 45%); $\nu_{max}$ (KBr) 3360, 3260, 1767, 1675, and 1616 cm⁻¹; $\delta_H$ (D₂O) (major rotamer) 1.91 (2H, complex m), 2.91 (2H, complex m), 3.12 and 3.56 (2H, ABq, J 17.5 Hz), 3.61 (2H, t, J 5.22 (1H, s), 5.25 and 5.37 (2H, ABq, J 14.6 Hz), 7.9–8.0 (1H, m), 8.14 (1H, s), 8.42 (1H, m), 8.72 (1H, m), and 8.79 (1H, s); [F.A.B. (Glycerol/H₂O) MH+393].

(b) 7β-[D-2-[(4-Ethyl-2,3-dioxopiperazin-1-yl)carbonyl amino]-2-phenylacetamido]-7α-formamido-3-[3-(3-hydroxypropyl)pyridinium]methyl-ceph-3-em 4-carboxylate 7β-Amino-7α-formamido-3-[3-(3-hydroxypropyl)-pyridinium]methyl-ceph-3-em-4-carboxylate (100 mg; 0.26 mmol) was suspended in anhydrous dichloromethane (5 ml), chlorotrimethylsilane (0.2 ml; 1.56 mmol) and N,N-dimethylaniline (0.26 ml; 2.08 mmol) added and the mixture refluxed under argon for 1h. To the resulting cooled solution was added D-2-[(4-ethyl-2,3-dioxopiperazin1-yl)carbonylamino]-2-phenylacetyl chloride (prepared from the corresponding acid (104 mg; 0.33 mmol) as described in Example 1(b)) in anhydrous dichloromethane (0.5 ml) at room temperature. After 1.5 h the title product (63 mg; 36%) (containing ca. 15% L isomer) was isolated as described in Example 1(c); $\lambda_{max}$ (H₂O) 259 nm ($\epsilon_m$ 16078); $\nu_{max}$ (KBr) 3400, 3300, 1783, 1710, 1676, and 1616 cm⁻¹; $\delta_H$ (D₂O) (D isomer; major rotamer) inter alia 1.16 (3H, t, J 7 Hz), 1.90 (2H, m), 2.80 and 3.39 (2H, ABq, J 17.6 Hz), 2.85 (2H, m), 3.47 (2H, q, J 7 Hz), 3.5–3.7 (4H, m), 3.9–4.1 (2H, m), 5.1–5.4 (2H, m, overlaps δ.31, 1H, s), 5.46 (1H, s), 7.3–7.6 (5H, m), 7.9 (1H, m), 8.13 (1H, s), 8.4 (1H, m), 8.7 (1H, m), and 8.75 (1H, s); [F.A.B. (Glycerol/H$_2$O) MH$^+$ 694].

EXAMPLE 13

3-(3-Acetylpyridinium)methyl-7β-amino-7α-formamido-ceph-3-em-4-carboxylate

7β-Amino-7α-formamidocephalosporanic acid (0.3 g; 0.94 mmol) was reacted with sodium iodide (1.269 g; 8.46 mmol) and 3-acetylpyridine (0.48 ml; 4.34 mmol) in water (1 ml) at 60° C. for 6 h as described in Example 2(a) to give the title compound (0.122 g; 34%); ν$_{max}$ (KBr) 3422, 1761, 1700 (sh), 1673, and 1615 cm$^{-1}$; δ$_H$ (D$_2$O) (major rotamer) 2.81 (3H, s), 3.22 and 3.68 (2H, ABq, J 17.6 Hz), 5.29 (1H, s), 5.41 and 5.47 (2H, ABq, J 14.7 Hz), 8.20 (1H, s), 8.29 (1H, m), 9.08 (1H, m), 9.18 (1H, m), and 9.59 (1H, s).

EXAMPLE 14

7β-[D-2-[(4-Ethyl-2,3-dioxopiperazin-1-yl)carbonyl amino]-2-phenylacetamido]-7α-formamido-3-(4-phenyl pyridinium)methyl-ceph-3-em-4-carboxylate (a) 7β-Amino-7α-formamido-3-(4-phenylpyridinium) methyl-ceph-3-em 4-carboxylate 7β-Amino-7α-formamidocephalosporanic acid (0.2 g; 0.64 mmol) in water (6 ml) was reacted with sodium iodide (0.846 g; 5.64 mmol) and 4-phenylpyridine (0.437 g; 2.81 mmol) as described in Example 2(a) to give the title product (0.066 g; 26%); ν$_{max}$ (KBr) 3373, 1770, 1676, 1637, and 1620 cm$^{-1}$; δ$_H$ (D$_2$O) (major rotamer) 3.19 and 3.61 (2H, ABq, J 17.6 Hz), 5.26 (1H, s), 5.28 and 5.40 (2H, ABq, J 14.6 Hz), 7.55–7.7 (3H, m), 7.85–8.0 (2H, m), 8.16 (1H, s), 8.30 (2H, d, J 6 Hz), and 8.85 (2H, d, J 6 Hz); [F.A.B. (Glycerol/Dimethylsulphoxide) MH$^+$ 411].

(b) 7β-[D-2-[(4-Ethyl-2,3-dioxopiperazin-1-yl)carbonyl amino]-2-phenylacetamido]-7α-formamido-3-(4-phenylpyridinium)methyl-ceph-3-em-4-carboxylate 7β-Amino-7α-formamido-3-(4-phenylpyridinium)-methyl-ceph-3-em 4-carboxylate (60 mg; 0.146 mmol) was suspended in anhydrous dichloromethane (5 ml) containing chlorotrimethylsilane (0.11 ml; 0.99 mmol) and N,N-dimethylaniline (0.15 ml; 1.18 mmol) and the mixture refluxed for 1h under argon. The resulting solution was cooled to room temperature and a solution of D-2-[(4-ethyl-2,3-dioxopiperazin-1-yl)carbonylamino]-2-phenylacetyl chloride (prepared from the corresponding acid (58 mg; 1.82 mmol) as described in Example 1(b)) in anhydrous dichloromethane (0.5 ml) added. After ca. 40 min, the title product (23 mg; 22%) (containing ca. 20% L isomer) was isolated as described in Example 1(c); λ$_{max}$ (H$_2$O) 294 nm (ε$_m$ 20045); ν$_{max}$ (KBr) 3404, 3300, 1781, 1710 (sh), 1679, and 1634 cm$^{-1}$; δ$_H$ (D$_2$O) (D isomer; major rotamer) inter alia 1.11 (3H, t, J 7 Hz), 2.85 (1H, higher field arm of ABq, J 18 Hz), 3.3–3.7 (5H, complex m), 3.8–3.9 (2H, m), 5.11 (1H, higher field arm of ABq, J 15.2 Hz; lower field arm obscured), 5.34 (1H, s), 5.44 (1H, s), 7.1–7.5 (5H, m), 7.5–7.7 (3H, m), 7.8–7.9 (2H, m), 8.05–8.3 (3H, m), and 8.75–8.85 (2H, m); [F.A.B. (Glycerol/H$_2$O) MH$^+$ 712].

EXAMPLE 15

7β-Amino-3-(3-carbamoylpyridinium)methyl-7α-formamido-ceph-3-em-4-carboxylate

7β-Amino-7α-formamidocephalosporanic acid (0.43 g; 1.36 mmol), nicotinamide (0.244 g; 2 mmol) and sodium iodide (2.4 g; 15.9 mmol) were dissolved in water (10 ml) and the pH adjusted to 6.5 with 2M sodium hydroxide solution. The mixture was heated at 60° C. under argon for 5 h, cooled and the pH readjusted to 6.5 with 2M sodium hydroxide solution. Chromatography on HP20SS resin and lyophilisation of the product containing fractions afforded the title product (0.138 g; 26%); λ$_{max}$ 261 nm (ε$_m$ 12120); ν$_{max}$ (KBr) 3340, 1765, 1675, and 1610 cm$^{-1}$; δ$_H$ (D$_2$O) (major rotamer) 3.18 and 3.63 (2H, Abq, J 17.6z), 5.26 (1H, s), 5.38 and 5.51 (2H, ABq, J 14.6 Hz), 8.15 (1H, s), 8.22 (1H, m), 8.93 (1H, m), 9.11 (1H, m), and 9.38 (1H, s).

EXAMPLE 16

3-(2,3-Cyclohexenopyridinium)methyl-7β-[D-2-[(4-ethyl-2,3-dioxopiperazin-1-yl)carbonylamino]-2-phenyl acetamido]-7α-formamido-ceph-3-em-4-carboxylate (a)

7β-Amino-3-(2,3-cyclohexenopyridinium)methyl-7α-formamido-ceph-3-em-4-carboxylate 7β-Amino-7α-formamidocephalosporanic acid (0.2 g; 0.64 mmol) was suspended in water (5 ml) and sodium iodide (0.846 g; 5.64 mmol) and 2,3-cyclohexenopyridine (0.375 g; 2.81 mmol) added. Acetone was added to give a homogeneous solution which was heated at 60° C. for 6 h under argon. Purification of the reaction mixture as described in Example 2(a) gave the title product (0.075 g; 32%); ν$_{max}$ (KBr) 3369, 1771, 1675, and 1615 cm$^{-1}$; δ$_H$(D$_2$O) (major rotamer) 1.8–2.1 (4H, complex m), 2.9–3.15 (4H, 2 complex m's), 3.16 and 3.48 (2H, ABq, J 10.5 Hz; higher field arm partially obscured by m, δ2.9–3.15), 5.23 and 5.43 (2H, ABq, J 15.5 Hz), 5.25 (1H, s), 7.76 (1H, m), 8.18 (1H, s), 8.23 (1H, m), and 8.57 (1H, m); [F.A.B. (Glycerol/H$_2$O) MH$^+$ 389].

(b)

3-(2,3-Cyclohexenopyridinium)methyl-7β-[D-2-([4-ethyl-2,3-dioxopiperazin-1-yl]carbonylamino)-2-phenylacetamido]-7α-formamido-ceph-3-em-4-carboxylate 7β-Amino-3-(2,3-cyclohexenopyridinium)methyl-7α-formamido-ceph-3-em-4-carboxylate (120 mg; 0.32 mmol) was suspended in anhydrous dichloromethane (5 ml) containing chlorotrimethylsilane (0.24 ml; 1.92 mmol) and N,N-dimethylaniline (0.32 ml; 2.56 mmol) and the mixture refluxed for 15 min under argon. To the resulting cooled solution was added D-2-[(4-ethyl-2,3-dioxopiperazin-1-yl)carbonylamino]-2-phenylacetyl chloride (prepared from the corresponding acid (86 mg; 0.27 mmol) as described in Example 1(b)) in anhydrous dichloromethane (0.5 ml) at room temperature. After ca. 40 min the title product (47 mg; 22%) (containing ca. 25% L-isomer) was isolated as described in Example 1(c); ν$_{max}$ KBr) 3421, 1777, 1710, 1676, and 1612 cm$^{-1}$; δ$_H$(D$_2$O) (D isomer; major rotamer) inter alia 1.16 (3H, t, J 7 Hz), 1.7–2.0 (4H, 2 complex m's), 2.79 and 3.23 (2H, ABq, J 18 Hz), 2.85–3.1 (4H, m), 3.47 (2H, q, J 7 Hz), 3.66 (2H, broad s), 3.97 (2H, m), 5.20 and 5.40 (2H, ABq, J 16 Hz), 5.32 (1H, s), 5.49 (1H, s), 7.3–7.5 (5H, m), 7.6–7.8 (1H, m), 8.13 (1H, s), 8.19 (1H, m), and 8.43 (1H, m); [F.A.B. (Thioglycerol/H₂O) MH+ 690].

EXAMPLE 17

7β-[D-2-[(4-Ethyl-2,3-dioxopiperazin-1-yl)carbonylamino]-2-phenylacetamido]-7α-formamido-3-(3-methoxy pyridinium)methyl-ceph-3-em-4-carboxylate (a) 7β-Amino-7α-formamido-3-(3-methoxypyridinium)methyl-ceph-3-em-4-carboxylate 7β-Amino-7α-formamidocephalosporanic acid (0.2 g; 0.64 mmol) was heated with sodium iodide (0.846 g; 5.64 mmol) and 3-methoxypyridine (0.367 g; 3.37 mmol) in water at 60° C. under argon for 6 h. Purification of the reaction mixture as described in Example 2(a) afforded the title product (0.109 g; 47%); $\nu_{max}$ (KBr) 3369, 1766, 1676, and 1610 cm⁻¹; $\delta_H$ (D₂O) (major rotamer) 3.16 and 3.61 (2H, ABq, J 17.6 Hz), 4.03 (3H, s), 5.26 (1H, s), 5.26 and 5.41 (2H, ABq, J 14 Hz), 7.98 (1H, m), 8.13 (1H, m), 8.17 (1H, s), 8.53 (1H, m), and 8.69 (1H, s).

(b) 7β-[D-2-[(4-Ethyl-2,3-dioxopiperazin-1-yl)carbonylamino]-2-phenylacetamido]-7α-formamido-3-(3-methoxypyridinium)methyl-ceph-3-em-4-carboxylate 7β-Amino 7α-formamido-3-(3-methoxypyridinium)-methyl-ceph-3-em-4-carboxylate (91 mg; 0.25 mmol) was suspended in anhydrous dichloromethane (5 ml) containing chlorotrimethylsilane (0.19 ml; 1.5 mmol) and N,N-dimethylaniline (0.33 ml; 2.6 mmol) and the mixture refluxed for 0.75 h under argon. The resulting solution was cooled to room temperature and D-2-[(4-ethyl-2,3-dioxopiperazin-1-yl)carbonylamino]-2-phenylacetyl chloride (prepared from the corresponding acid (120 mg; 0.37 mmol) as described in Example 1(b)) added in anhydrous dichloromethane (1 ml). After stirring at room temperature for ca. 0.75 h, the title product (106 mg; 64%) (containing ca. 20% L-isomer) was isolated as described in Example 1(c); $\lambda_{max}$ (H₂O) 250 nm ($\epsilon_m$ 12469); $\nu_{max}$ (KBr) 3431, 1780, 1710, 1675, and 1611 cm⁻¹; $\delta_H$ (D₂O) (D isomer; major rotamer) inter alia 1.18 (3H, t, J 7 Hz), 2.83 (1H, higher field arm of ABq, J 17 Hz), 3.48 (2H, q, J 7 Hz) (obscures ca. 63.43 (1H, lower field arm of ABq)), 3.67 (2H, broad s), 3.97 (3H, s), overlaps 3.9–4.1 (2H, m), 5.35 (1H, s), 5.52 (1H, s), 7.3–7.5 (5H, m), 7.95 (1H, m), 8.11 (1H, m), 8.15 (1H, s), 8.47 (1H, m), and 8.66 (1H, s); [F.A.B. (Glycerol/H₂O) MH+ 666].

EXAMPLE 18

7β-Amino-3-(3-chloropyridinium)methyl-7α-formamido-ceph-3-em-4-carboxylate

To 7β-amino-7α-formamidocephalosporanic acid (100 mg; 0.31 mmol) in water (6 ml) was added sodium iodide (670 mg; 4.47 mmol) and 3-chloropyridine (778 mg; 4.21 mmol). Acetone was added to give an homogeneous solution and the pH adjusted to 6.5 by the addition of saturated aqueous sodium hydrogen carbonate solution. The mixture was heated at 60° C. and the reaction monitored by reverse phase HPLC. After ca. 7 h purification as in Example 2(a) gave the title compound (25 mg; 21%); $\nu_{max}$ (KBr) 3365, 3280 (sh), 1763, 1671, and 1609 cm⁻¹; $\delta_H$ (D₂O) (major rotamer) 3.17 and 3.64 (together 2H, ABq, J 17.4 Hz), 5.27 (1H, s), 5.31 and 5.47 (together 2H, ABq, J 15.5 Hz), 8.09 (1H, dd, J 8.1 and 7.0 Hz), 8.17 (1H, s), 8.63 (1H, d, J 8.1 Hz), 8.93 (1H, d, J 7.0 Hz), and 9.16 (1H, s).

EXAMPLE 19

7β-[D-2-(3,4-Diacetoxyphenyl)-2-[(4-ethyl-2,3-dioxopiperazin-1-yl)carbonylamino]acetamido]-7α-formamido-3-(quinolinium)methyl-ceph-3-em-4-carboxylate (a) 7β-Amino-7α-formamido-3-(quinolinium)methyl-ceph-3-em-4-carboxylate To 7β-amino-7α-formamidocephalosporanic acid (0.6 g; 1.90 mmol) in water (15 ml) was added sodium iodide (2.52 g; 16.8 mmol) and quinoline (1.08 g, 8.4 mmol). Acetone was added, with stirring, to give an homogeneous solution, and the mixture heated at 60° C. for ca. 6.5 h (reaction monitored by reverse phase HPLC). Purification as in Example 2(a) afforded the title compound (0.113 g; 15%); $\nu_{max}$ (KBr) 3373, 3240 (sh), 1772, 1668, and 1616 cm⁻¹; $\delta_H$ (D₂O) 3.14 and 3.42 (together 2H, ABq, J 17.6 Hz), 5.19 (1H, s), 5.74 and 5.93 (together 2H, ABq, J 15.4 Hz), 7.90–8.13 (2H, m), 8.15 (1H, s), 8.18–8.55 (3H, m), and 9.05–9.30 (2H, m).

(b) 7β-[D-2-(3,4-Diacetoxyphenyl)-2-[(4-ethyl-2,3-dioxopiperazin-1-yl)carbonylamino]acetamido]-7α-formamido-3-(quinolinium)methyl-ceph-3-em-4-carboxylate 7β-Amino-7α-formamido-3-(quinolinium)methyl-ceph-3-em-4-carboxylate (126 mg; 0.33 mmol) was acylated as in Example 2(c) with D-2-(3,4-diacetoxyphenyl)-2-[(4-ethyl-2,3-dioxopiperazin-1-yl)carbonylamino]acetyl chloride (freshly prepared from the corresponding acid (214 mg; 0.49 mmol) via the method in Example 2(b)) to give the title compound (110 mg; 42%, containing ca. 30% L isomer); $\nu_{max}$ (KBr) 3400, 3290, 1773, 1710 (sh), 1675, and 1625 cm⁻¹; $\delta_H$ (D₂O) (D isomer; major rotamer) inter alia 1.19 (3H, t, J 7.4 Hz), 2.10–2.40 (6H, m), 2.56 and 3.13 (together 1.4H, ABq, J 17 Hz), 3.35–3.60 (2H, m), 3.60–3.80 (2H, m), 3.85–4.10 (2H, m), 5.32 (0.7H, s), 5.50 (0.7H, s), 5.65–6.00 (2H, m), 6.95–7.55 (3H, m), 7.90–8.60 (6H, m), and 9.00–9.30 (2H, m); [F.A.B. (+ve ion) (H20/Dimethylsulphoxide/Glycerol) MH+ 802].

EXAMPLE 20

3-[4-(tert.-Butyl)pyridinium]methyl-7β-[D-2-[(4-ethyl-2,3-dioxopiperazin-1-yl)carbonylamino]-2-phenyl acetamido]-7α-formamido-ceph-3-em-4-carboxylate (a) 7β-Amino-3-[4-(tert.-butyl)pyridinium]methyl-7α-formamido-ceph-3-em-4-carboxylate 7β-Amino-7α-formamidocephalosporanic acid (0.3 g; 0.95 mmol) was reacted with 4-(tert.-butyl)pyridine (0.567 g; 4.2 mmol) and sodium iodide (1.26 g; 8.4 mmol) as described in Example 2(a) to give the title compound (0.145 g; 39%); $\lambda_{max}$ (H₂O) 228 ($\epsilon_m$ 11951) and 255 nm (13240); $\nu_{max}$ (KBr) 3377, 3280 (sh), 1764, 1674, 1640 (sh), and 1615 cm⁻¹; $\delta_H$ (D₂O) 1.39 (9H, s), 3.13 and 3.56 (together 2H, ABq, J 17.6 Hz), 5.24 and 5.36 (together 2H, ABq, J 14.6 Hz), 5.24 (1H, s), 8.08 (2H, d, J 6.7 Hz), 8.16 (1H, s), and 8.75 (2H, d, J 6.7 Hz); [F.A.B. (+ve ion) (Thioglycerol) MH+ 391].

(b) 3-[4-(tert.-Butyl)pyridinium]methyl-7β-[D-2-[(4-ethyl-2,3-dioxopiperazin-1-yl)carbonylamino]-2-phenylacetamido]-7α-formamido-ce-ph-3-em-4-carboxylate 7β-Amino-3-[4-tert.-butyl)pyridinium]methyl-7α-formamido-ceph-3-em-4-carboxylate (117 mg; 0.3 mmol) was acylated as described in Example 2(c) with D-2-[(4-ethyl-2,3-dioxopiperazin-1-yl)carbonylamino]-2-phenyl acetyl chloride (freshly prepared from the corresponding acid (144 mg, 0.45 mmol) via the method described in Example 1(b)) to give the title compound (137 mg; 66%); $\lambda_{max}$ (H$_2$O) 226 ($\epsilon_m$ 21282) and 255 nm (13240); $\nu_{max}$ (KBr) 3410, 3290, 1780, 1710 (sh), 1683, 1635, and 1616 cm$^{-1}$; $\delta_H$ (D$_2$O) (D-isomer; major rotamer) 1.15 (3H, t, J 7.1 Hz), 1.38 (9H, s), 2.75 and 3.36 (together 2H, ABq, J 17.7 Hz), 3.47 (2H, q, J 7.1 Hz), 3.55–3.75 (2H, m), 3.80–4.10 (2H, m), 5.12 and 5.30 (together 2H, ABq, J 14.4 Hz), 5.31 (1H, s), 5.47 (1H, s), 7.20–7.55 (5H, m), 8.04 (2H, d, J 6.2 Hz), 8.12 (1H, s), and 8.68 (2H, d, J 6.2 Hz); [F.A.B. (+ve ion) (Thioglycerol) MH+ 692].

EXAMPLE 21

7β-[D-2-[(4-(3-Chlorophenyl)-2,3-dioxopiperazin-1-yl) carbonylamino]-2-phenylacetamido]-3-(4-ethylpyridinium) methyl-7α-formamido-ceph-3-em-4-carboxylate 7β-Amino-3-(4-ethylpyridinium)methyl-7α-formamido-ceph-3-em-4-carboxylate (87 mg; 0.24 mmol) was acylated as in Example 2(c) with D-2-[(4-(3-chlorophenyl)-2,3-dioxopiperazin-1-yl)carbonylamino]-2-phenylacetyl chloride (freshly prepared from the corresponding acid (120 mg, 0.30 mmol) as in Example 1(b)) to give the title compound (24 mg; 13%); $\nu_{max}$ (KBr) 3400, 3310 (sh), 1777, 1710 (sh), 1683, 1640, and 1620 cm$^{-1}$; $\delta_H$ [1:1 (CD$_3$)$_2$CO/D$_2$O] (D isomer; major rotamer) 1.37 (3H, t, J 7.3 Hz), 2.89 and 3.51 (together 2H, ABq, J 17.5 Hz), 2.95–3.10 (2H, m), 4.00–4.35 (4H, m), 5.15–5.70 (4H, m), 7.30–7.70 (9H, m), 7.90–8.10 (2H, m), 8.21 (1H, s), and 8.75–9.00 (2H, m); [F.A.B. (+ve ion) (Thioglycerol) MH+ 746].

EXAMPLE 22

7β-[D-2-[(4-Ethyl-2,3-dioxopiperazin-1-yl)carbonyl amino]-2-phenylacetamido]-7α-formamido-3-(4-methoxy pyridinium)methyl-ceph-3-em-4-carboxylate (a) 7β-Amino-7α-formamido-3-(4-methoxypyridinium) methyl-ceph-3-em-4-carboxylate 7β-Amino-7α-formamidocephalosporanic acid (0.331 g; 1.05 mmol) was reacted with 4-methoxypyridine (0.504 g; 4.62 mmol) and sodium iodide (1.39 g; 9.3 mmol) as described in Example 2(a) to give the title compound (0.154 g; 40%); $\lambda_{max}$ (H$_2$O) 245 nm ($\epsilon_m$ 15427); $\nu_{max}$ (KBr) 3370, 3280 (sh), 1766, 1674, 1637, and 1615 cm$^{-1}$; $\delta_H$(D$_2$O) (major rotamer) 3.16 and 3.58 (together 2H, ABq, J 17.6 Hz), 4.11 (3H, s), 5.11 and 5.22 (together 2H, ABq, J 14.5 Hz), 5.23 (1H, s), 7.35–7.55 (2H, m), 8.16 (1H, s), and 8.50–8.70 (2H, m); [F.A.B. (+ve ion) (Glycerol/H$_2$O) MH+ 365].

(b) 7β-[D-[(4-Ethyl-2,3-dioxopiperazin-1-yl)carbonyl amino]-2-phenylacetamido]-7α-formamido-3-(4-methoxypyridinium)methyl-ceph-3-em-4-carboxylate 7β-Amino-7α-formamido-3-(4-methoxypyridinium)-methyl-ceph-3-em-4-carboxylate (91 mg; 0.25 mmol) was acylated as in Example 2(c) with D-2-[(4-ethyl-2,3-dioxopiperazin-1-yl)carbonylamino]-2-phenylacetyl chloride (freshly prepared from the corresponding acid (100 mg; 0.313 mmol) via the method in Example 1(b)) to give the title compound (70 mg; 42%); $\lambda_{max}$ (H$_2$O) 244 nm ($\epsilon_m$ 21071); $\nu_{max}$ (KBr) 3411, 1779, 1710 (sh), 1675, 1640, and 1620 (sh) cm$^{-1}$; $\delta_H$ (D$_2$O) (major rotamer) 1.18 (3H, t, J 7.1 Hz), 2.85 (1H, higher field arm of ABq, J 17.3 Hz), 3.35–3.75 (5H, m), 3.80–4.04 (2H, m), 4.12 (3H, s), 5.02 and 5.17 (together 2H, ABq, J 14.7 Hz), 5.33 (1H, s), 5.52 (1H, s), 7.25–7.60 (7H, m), 8.15 (1H, s), and 8.45–8.70 (2H, m); [F.A.B. (+ve ion) (Glycerol/H$_2$O) MH+ 666].

EXAMPLE 23

7β-Amino-3-(4-carbamoylpyridinium)methyl-7α-formamido-ceph-3-em-4-carboxylate

To 7β-amino-7α-formamidocephalosporanic acid (215 mg; 0.68 mmol) in water (7 ml) was added 4-carbamoylpyridine (122 mg, 1.0 mmol) and sodium iodide (800 mg; 5.33 mmol). The pH of the mixture was adjusted to 6.5 by the addition of M sodium hydroxide solution. The mixture was heated at 60° C.; the reaction was monitored by reverse phase HPLC. After ca. 3.5 h the mixture was cooled to room temperature and the pH readjusted to 6.5 with M sodium hydroxide solution. Chromatography on HP20SS resin, eluting initially with water then acetone/water mixtures, followed by lyophilisation afforded the title compound (90 mg; 35%); $\nu_{max}$ (KBr) 3300, 1760, 1670, and 1600 cm$^{-1}$; $\delta_H$ (D$_2$O) 3.20 and 3.70 (together 2H, ABq, J 18 Hz), 5.30 (1H, s), 5.50 (2H, AA' system), 8.20 (1H, s), 8.42 (2H, d, J 7 Hz), and 9.13 (2H, d, J 7 Hz); [F.A.B. (+ve ion) (Thioglycerol/H$_2$O) MH+378].

EXAMPLE 24

7β-Amino-7α-formamido-3-(isoquinolinium)methyl-ceph-3-em-4-carboxylate

7β-Amino-7α-formamidocephalosporanic acid (0.50 g; 1.59 mmol) was reacted with isoquinoline (1.203 g, 9.3 mmol) and sodium iodide (2.80 g, 18.7 mmol) as described in Example 2(a) to give the title compound (0.082 g; 13%); $\nu_{max}$ (KBr) 3350, 3280 (sh), 1766, 1670, and 1611 cm$^{-1}$; $\delta_H$(D$_2$O) (major rotamer) 3.20 and 3.61 (together 2H, ABq, J 17.7 Hz), 5.26 (1H, s), 5.45 and 5.56 (together 2H, ABq, J 14.5 Hz), 7.95–8.10 (1H, m), 8.17 (1H, s), 8.20–8.30 (2H, m), 8.35–8.50 (2H, m), 8.50–8.65 (1H, m), and 9.75 (1H, s); [F.A.B. (+ve ion) (Thioglycerol/MeOH) MH+ 385].

EXAMPLE 25

7β-[D-2-[(4-Ethyl-2,3-dioxopiperazin-1-yl)carbonyl amino]-2-phenylacetamido]-7α-formamido-3-[4-(prop-1-yl)pyridinium]methyl-ceph-3-em-4-carboxylate (a) 7β-Amino-7α-formamido-3-[4-(prop-1-yl)pyridinium]-methyl-ceph-3-em-4-carboxylate 7β-Amino-7α-formamidocephalosporanic acid (0.284 g; 0.95 mmol) was reacted with 4-(prop-1-yl)pyridine (0.721 g; 5.95 mmol) and sodium iodide (1.05 g; 7.00 mmol) as described in Example 2(a) to give the title compound (0.135 g; 37%); $\lambda_{max}$ (H$_2$O) 227 ($\epsilon_m$ 12187) and 255 nm (13475); $\nu_{max}$ 3360, 3280, 1770, 1676, 1645 (sh), and 1615 cm$^{-1}$; $\delta_H$ (D$_2$O) (major rotamer) 0.92 (3H, t, J 7.4 Hz), 1.72 (2H, tq, J 7.5 and 7.4 Hz), 2.89 (2H, t, J 7.5 Hz), 3.3 and 3.56 (together 2H, ABq, J 17.6

Hz), 5.22 and 5.33 (together 2H, Abq, J 14.7 Hz), 5.23 (1H, s), 7.89 (2H, d, J 6.4 Hz), 8.14 (1H, s), and 8.70 (2H, d, J 6.4 Hz); [F.A.B. (+ve ion) (Thioglycerol) MH+ 377].

(b) 7β-[D-2-[(4-Ethyl-2,3-dioxopiperazin-1-yl)carbonyl amino]-2-phenylacetamido]-7α-formamido.3-[4-(prop-1 yl)pyridinium]methyl-ceph-3-em.4-carboxylate 7β-Amino 7α-formamido-3-[4-(prop-1-yl)pyridinium]methyl -ceph-3-em-4-carboxylate (117 mg; 0.31 mmol) was acylated as described in Example 2(c) with D-2-[(4-ethyl-2,3-dioxopiperazin-1-yl)carbonylamino]-2-phenylacetyl chloride (freshly prepared from the corresponding acid (124 mg; 0.39 mmol) via the method described in Example 1(b)) to give the title compound (111 mg; 53%) (containing ca. 5% of the L isomer); $\nu_{max}$ (KBr) 3400, 3290, 1779, 1710 (sh), 1676, 1640, and 1615 cm$^{-1}$; $\delta_H$ (D$_2$O) (D isomer; major rotamer) 0.92 (3H, t, J 7.0 Hz), 1.16 (3H, t, J 7.0 Hz), 1.60–1.90 (2H, m), 2.78 and 3.38 (together 2H, ABq, J 17.5 Hz), 2.83–3.05 (2H, m), 3.40–3.58 (2H, m), 3.60–3.80 (2H, m), 3.82–4.15 (2H, m), 5.11 and 5.29 (together 2H, ABq, J 14.8 Hz), 5.31 (1H, s), 5.47 (1H, s), 7.25–7.60 (5H, m), 7.75–8.00 (2H, m), 8.13 (1H, s), and 8.60–8.80 (2H, m); [F.A.B. (+ve ion) (Thioglycerol) MH+ 678].

EXAMPLE 26

7β-[D-2-[(4-Ethyl-2,3-dioxopiperazin-1-yl)carbonyl amino]-2-phenylacetamido]-3-(2-ethylpyridinium)methyl-7α-formamido-ceph-3-em-4-carboxylate

(a)
7β-Amino-3-(2-ethylpyridinium)methyl-7α-formamido-ceph-3-em-4-carboxylate 7β-Amino 7α-formamidocephalosporanic acid (200 mg, 0.64 mmol) in water (8 ml) was reacted with sodium iodide (670 mg, 4.47 mmol) and 2-ethylpyridine (428 mg, 4.0 mmol) as described in Example 1(a) to afford the title compound (54 mg; 23%); $\nu_{max}$ (KBr) 3366, 3280, 1772, 1675, and 1617 cm$^{-1}$; $\delta_H$ (D$_2$O) (major rotamer) 1.40 (3H, t, J 7.4 Hz), 3.10–3.25 (3H, m), 3.52 (1H, lower field arm of ABq, J 17.6 Hz), 5.25 (1H, s), 5.32 and 5.49 (together 2H, ABq, J 15.3 Hz), 7.85–8.05 (2H, m), 8.18 (1H, s), 8.40–8.52 (1H, m), and 8.70–8.80 (1H, m).

(b) 7β-[D-2-[(4-Ethyl-2,3-dioxopiperazin-1-yl)carbonyl amino]-2-phenylacetamido]-3-(2-ethylpyridinium) methyl-7α-formamido-ceph-3-em-4-carboxylate 7β-Amino 3-(2-ethylpyridinium)methyl-7α-formamido-ceph-3-em-4-carboxylate (91 mg, 0.25 mmol) in dry dichloromethane (5 ml) was reacted with N,N-dimethylaniline (242 mg, 2.0 mmol) and chlorotrimethylsilane (109 mg, 1.0 mmol) under argon at reflux. After 0.33 h a further quantity of chlorotrimethylsilane (55 mg, 0.5 mmol) was added and reflux continued for a further 0.4 h. To the resulting solution at ambient temperature was added D-2-[(4-ethyl-2,3-dioxopiperazin-1-yl)carbonylamino]-2-phenylacetyl chloride (freshly prepared from the corresponding acid (120 mg, 0.375 mmol) via the method described in Example 1(b)) in dry dichloromethane (5 ml). After ca. 0.5 h purification as described in Example 1(c) afforded the title compound (61 mg; 37%) (containing ca. 20% of the L-isomer); $\nu_{max}$ (KBr) 3420, 3290(sh), 1781, 1710(sh), 1677, and 1624 cm$^{-1}$; $\delta_H$ (D$_2$O) (D-isomer, major rotamer) 1.18 (3H, t, J 7.1 Hz), 1.35 (3H, t, J 7.2 Hz), 2.81 and 3.31 (together 2H, ABq, J 17.5 Hz), 3.11 (2H, q, J 7.2 Hz), 3.50 (2H, q, J 7.1 Hz), 3.60–3.80 (2H, m), 3.90–4.10 (2H, m), 5.20–5.50 (2H, m), 5.34 (1H, s), 5.50 (1H, s), 7.30–7.60 (5H, m), 7.80–8.05 (2H, m), 8.15 (1H, s), 8.40–8.55 (1H, m), and 8.55–8.70 (1H, m); [F.A.B. (+ve ion) (thioglycerol) MH+ 664].

EXAMPLE 27

7β-[D-2-[(4-Ethyl-2,3-dioxopiperazin-1-yl)carbonyl amino]-2-phenylacetamido]-3-(3-ethylpyridinium)methyl-7α-formamido-ceph-3-em-4-carboxylate

(a)
7β-Amino-3-(3-ethylpyridinium)methyl-7α-formamido-ceph-3-em-4-carboxylate 7β-Amino-7α-formamidocephalosporanic acid (200 mg, 0.64 mmol) in water (8 ml) was reacted with sodium iodide (670 mg, 4.47 mmol) and 3-ethylpyridine (428 mg, 4.0 mmol) as described in Example 1(a) to afford the title compound (110 mg, 47%); $\nu_{max}$ (KBr) 3370, 3270, 1770, 1675, and 1611 cm$^{-1}$; $\delta_H$ (D$_2$O) (major rotamer) 1.30 (3H, t, J 7.6 Hz), 2.89 (2H, q, J 7.6 Hz), 3.16 and 3.59 (together 2H, ABq, J 17.6 Hz), 5.25 (1H, s), 5.28 and 5.40 (together 2H, ABq, J 15.0 Hz), 7.98 (1H, dd, J 8.1 and 6.1 Hz), 8.17 (1H, s), 8.44 (1H, d, J 8.1 Hz), 8.74 (1H, d, J 6.1 Hz), and 8.79 (1H, s); [F.A.B. (+ve ion) (diamylphenol/CHCl3) MH+ 363].

(b) 7β-[D-2-[(4-Ethyl-2,3-dioxopiperazin-1-yl)carbonyl amino]-2-phenylacetamido]-3-(3-ethylpyridinium) methyl-7α-formamido-ceph-3-em-4-carboxylate 7β-Amino-3-(3-ethylpyridinium)methyl-7α-formamido-ceph-3-em 4-carboxylate (91 mg, 0.25 mmol) in dry dichloromethane (7 ml) was reacted with N,N-dimethylaniline (242 mg, 2.0 mmol) and chlorotrimethylsilane (109 mg, 1.0 mmol) under argon at reflux for 0.5 h. To the resulting solution at ambient temperature was added D-2-[(4-ethyl-2,3-dioxopiperazin-1-yl)carbonylamino]-2-phenylacetyl chloride (freshly prepared from the corresponding acid (120 mg, 0.375 mmol) via the method described in Example 1(b)) in dry dichloromethane (ca. 5 ml). After ca. 0.5 h purification as described in Example 1(c) afforded the title compound (86 mg; 52%) (containing ca. 25% L-isomer); $\nu_{max}$ (KBr) 3423, 3300(sh), 1780, 1710(sh), 1680, and 1615 cm$^{-1}$; $\delta_H$ (D$_2$O) (D-isomer, major rotamer) 1.18 (3H, t, J 7.1 Hz), 1.24–1.35 (3H, m), 2.75–3.00 (3H, m), 3.35–3.58 (3H, m), 3.60–3.80 (2H, m), 3.85–4.10 (2H, m), 5.10–5.55 (4H, m), 7.25–7.55 (5H, m), 7.90–8.05 (1H, m), 8.15 (1H, s), 8.43 (1H, d, J 8.4 Hz), 8.68 (1H, d, J 5.4 Hz) and 8.73 (1H, s); [F.A.B. (+ve ion) (thioglycerol) MH+ 664].

EXAMPLE 28

Sodium 7β-Amino-7α-formamido-3-[4-(2-sulfoethyl) pyridinium]methyl-ceph-3-em-4-carboxylate A mixture of 7β-amino-7α-formamidocephalosporanic acid, (0.215 g, 0.68 mmol), 4-(2-sulfoethyl)pyridine (0.187 g, 1.0 mmol) and sodium iodide (1.65 g, 11.0 mmol) in water (10 ml) was adjusted to pH 6.5 by the addition of 2.5M aqueous sodium hydroxide solution. The resulting solution was heated to 60° C. for ca. 6 h, then cooled and concentrated to ca. 6 ml. The concentrate was added dropwise to vigorously stirred acetone (100 ml). The precipitate was filtered off and washed with more acetone, then dried in vacuo. The solid was dissolved in water and chromatographed on HP20SS resin eluting with water to give the title compound (74 mg, 23%); $\nu_{max}$ (KBr) 3425, 3280(sh), 1760, 1670, 1610, 1190, and 1046 cm$^{-1}$; $\delta_H$ (D$_2$O) (major rotamer) 3.15 and 3.60 (together 2H, ABq, J 18 Hz), 3.38 (4H, s), 5.25 (1H, s), 5.35 (2H, AA' system), 8.02 (2H, d, J 7 Hz), 8.19 (1H, s), and 8.80 (1H, d, J 7 Hz).

EXAMPLE 29

3-(4-Cyclopropylpyridinium)methyl-7β-[D-2-[(4-ethyl-2,3-dioxopiperazin-1-yl)carbonylamino]-2-phenyl acetamido]-7α-formamido-ceph-3-em-4-carboxylate (a)

7β-Amino-3-(4-cyclopropylpyridinium)methyl-7α-formamido-ceph-3-em-4-carboxylate

7β-Amino-7α-formamidocephalosporanic acid (0.30 g, 0.95 mmol) in water (10 ml) was reacted with sodium iodide (1.26 g, 8.4 mmol) and 4-cyclopropylpyridine (0.50 g, 4.2 mmol) as described in Example 1(a) to afford the title compound (160 mg, 45%); $\lambda_{max}$ (H$_2$O) 257 nm ($\epsilon_m$ 19926); $\nu_{max}$ (KBr) 3410, 3280(sh), 1766, 1675, 1635, and 1610 cm$^{-1}$; $\delta_H$ (D$_2$O) (major rotamer) 1.08–1.24 (2H, m), 1.40–1.51 (2H, m), 2.20–2.30 (1H, m), 3.13 and 3.56 (2H, ABq, J 17.6 Hz), 5.17 and 5.28 (2H, ABq, J 15.4 Hz), 5.24 (1H, s), 7.66 (2H, d, J 6.9 Hz), 8.16 (1H, s), and 8.63 (2H, d, J 6.9 Hz); [F.A.B. (Thioglycerol) (+ve ion) MH+ 375].

(b)

3-(4-Cyclopropylpyridinium)methyl-7β-[D-2-[(4-ethyl-2,3-dioxopiperazin-1-yl)carbonylamino]-2-phenylacetamido]-7α-formamido-ceph-3-em 4-carboxylate 7β-Amino-3-(4-cyclopropylpyridinium)methyl-7α-formamido-ceph-3-em-4-carboxylate (75 mg, 0.2 mmol) in dry dichloromethane (10 ml) was reacted with N,N-dimethylaniline (194 mg, 1.6 mmol) and chlorotrimethyl silane (130 mg, 1.2 mmol) under argon at reflux for 0.25 h. To the resulting solution at ambient temperature was added D-2-[(4-ethyl-2,3-dioxopiperazin1-yl)carbonylamino]-2-phenylacetyl chloride (freshly prepared from the corresponding acid (96 mg, 0.3 mmol) via the method described in Example 1(b)) in dry dichloromethane (3 ml). After 0.66 h purification as described in Example 1(c) afforded the title compound (60 mg, 44%) (containing ca. 5% L-isomer); $\lambda_{max}$ (H$_2$O) 258 nm ($\epsilon_m$ 24858); $\nu_{max}$ (KBr) 3400, 3290, 1780, 1710(sh), 1680, 1635, and 1620 cm$^{-1}$; $\delta_H$ (D$_2$O) (D-isomer, major rotamer) 1.05–1.15 (5H, m), 1.37–1.55 (2H, m), 2.15–2.33 (1H, m), 2.78 and 3.37 (2H, ABq, J 17.6 Hz), 3.49 (2H, q, J 7.3 Hz), 3.58–3.77 (2H, m), 3.86–4.08 (2H, m), 5.05 and 5.24 (2H, ABq, J 14.6 Hz), 5.32 (1H, s), 5.48 (1H, s), 7.27–7.57 (5H, m), 7.62 2H, d, J 6.7 Hz), 8.14 (1H, s), and 8.53 (2H, d, J 7.6 Hz); [F.A.B. (Thioglycerol) (+ve ion) MH+ 676].

EXAMPLE 30

3-(4-Cyclopropylpyridinium)methyl-7β-[D-2-(3,4-diacetoxyphenyl)-2-[(4-ethyl-2,3-dioxopiperazin-1-yl) carbonylamino]acetamido]-7α-formamido-ceph-3-em-4-carboxylate 7β-Amino-3-(4-cyclopropylpyridinium)methyl-7α-formamido-ceph-3-em-4-carboxylate (73 mg; 0.195 mmol) was acylated as in Example 2(c) with D-2-(3,4-diacetoxyphenyl)-2-[(4-ethyl-2,3-dioxopiperazin-1-yl)carbonylamino]acetyl chloride (freshly prepared from the corresponding acid (125 mg; 0.293 mmol) via the method in Example 2(b)) to give the title compound (55 mg; 36%) (containing ca. 20% L isomer); $\lambda_{max}$ (H$_2$O) 259 nm ($\epsilon_m$ 25091); $\nu_{max}$ (KBr) 3434, 3280, 1772, 1710, 1676, 1635, and 1615 cm$^{-1}$; $\delta_H$ (D$_2$O) (D isomer, major rotamer) 1.17 (3H, t, J 7.2 Hz, obscuring 2H, m), 1.40–1.55 (2H, m), 2.15–2.40 (7H, m), 2.68 and 3.33 (2H, ABq, J 17.7 Hz), 3.49 (2H, q, J 7.4 Hz), 3.60–3.80 (2H, m), 3.85–4.10 (2H, m), 5.00–5.30 (2H, m), 5.33 (1H, s), 5.50 (1H, s), 7.20–7.55 (3H, m), 7.64 (2H, d, J 6.9 Hz), 8.15 (1H, s), and 8.53 (2H, d, J 6.8 Hz); [FAB (+ve ion) (thioglycerol) MH+ 792].

EXAMPLE 31

3-(4-Cyclopropylpyridinium)methyl-7β-[D-2-(3,4-dihydroxyphenyl)-2-[(4-ethyl-2,3-dioxopiperazin-1-yl) carbonylamino]acetamido]-7α-formamido-ceph-3-em-4-carboxylate 3-(4-Cyclopropylpyridinium)methyl-7β-[D-2-(3,4-diacetoxyphenyl)-2-[(4-ethyl-2,3-dioxopiperazin-1-yl)-carbonylamino]acetamido]-7α-formamido-ceph-3-em-4-carboxylate (42 mg; 0.053 mmol) in water (4 ml) was reacted with sodium sulphite (17 mg; 0.133 mmol) as in Example 3 to afford the title compound (21 mg; 56%) (containing ca. 20% L isomer); $\lambda_{max}$ (H$_2$O) 259 nm ($\epsilon_m$ 25182); $\nu_{max}$ (KBr) 3380 (sh), 3285, 1779, 1710 (sh), 1676, 1637, and 1615 (sh) cm$^{-1}$; $\delta_H$ (D$_2$O) (D isomer, major rotamer) 1.17 (3H, t, J 7.1 Hz, obscuring 2H, m), 1.35–1.55 (2H, m), 2.10–2.30 (1H, m), 2.82 (1H, lower field arm of ABq, J 16.3 Hz), 3.30–3.57 (3H, m), 3.57–3.80 (2H, m), 3.85–4.10 (2H, m), 5.05–5.45 (4H, m), 6.70–7.05 (3H, m), 7.50–7.70 (2H, m), 8.30 (1H, s), and 8.40–8.70 (2H, m); [FAB (+ve ion) (thioglycerol) MH+ 708].

EXAMPLE 32

7β-[D-2-[(4-Ethyl-2,3-dioxopiperazin-1-yl)carbonyl amino]-2-phenylacetamido]-7α-formamido-3-[4-(iso propyl)pyridinium]methyl-ce-ph-3-em-4-carboxylate (a) 7β-Amino-7α-formamido-3-[4-(isopropyl) pyridinium]methyl-ceph-3-em-4-carboxylate 7β-Amino-7α-formamidocephalosporanic acid (0.3 g; 0.95 mmol) was reacted with 4-(isopropyl)pyridine (0.508 g; 4.2 mmol) and sodium iodide (1.26 g; 8.4 mmol) as described in Example 2(a) to give the title compound (127 mg; 35%); $\lambda_{max}$ (H$_2$O) 226 ($\epsilon_m$ 11267), and 254 nm ($\epsilon_m$ 12141); $\nu_{max}$ (KBr) 3374, 3080 (sh), 1761, 1675, 1635, and 1610 cm$^{-1}$; $\delta_H$ (D$_2$O) (major rotamer) 1.33 (6H, d, J 6.8 Hz), 3.15 and 3.58 (2H, ABq, J 17.6 Hz), 3.24 (1H, septet, J 6.8 Hz), 5.25 and 5.36 (2H, ABq, J 14.6 Hz), 5.25 (1H, s), 7.96 (2H, d, J 6.7 Hz), 8.17 (1H, s), and 8.74 (2H, d, J 6.7 Hz); [FAB (+ve ion) (thioglycerol) MH+ 377, 2M+H+ 753].

(b) 7β-[D-2-[(4-Ethyl-2,3-dioxopiperazin-1-yl) carbonylamino]-2-phenylacetamido]-7α-formamido-3-[4-(isopropyl)pyridinium]methyl-ceph-3-em-4-carboxylate 7β-Amino-7α-formamido-3-[4-(isopropyl)pyridinium]methyl-ceph-3-em 4-carboxylate (127 mg; 0.338 mmol) in dry dichloromethane (10 ml) containing N,N-dimethylaniline (328 mg; 2.7 mmol) and trimethylchlorosilane (220 mg; 2.03 mmol) was stirred at room temperature for 1 h. A solution of D-2-[(4-ethyl-2,3-dioxopiperazin-1-yl)carbonylamino]-2-phenylacetyl chloride (freshly prepared from the corresponding acid (162 mg; 0.507 mmol) via the method described in Example 1(b)) in dry dichloromethane (0.75 ml) was added to the resulting solution at room temperature with stirring. After 1 h, the title compound (91 mg; 40%) (containing ca.10% L isomer) was isolated as described in Example 1(c); $\lambda_{max}$ (H$_2$O) 253 ($\epsilon_m$ 17210), and 225 nm ($\epsilon_m$ 21230); $\nu_{max}$ (KBr) 3412, 3290 (sh), 1779, 1710 (sh), 1678, and 1615 cm$^{-1}$; $\delta_H$ (D$_2$O) (major rotamer, D isomer) 1.16 (3H, t, J 7.2 Hz), 1.31 (6H, d, J 6.9 Hz), 2.77 and 3.38 (2H, ABq, J 17.6 Hz), 3.22 (1H, septet, J, 6.9 Hz), 3.48 (2H, q, J 7.2 Hz), 3.56–3.75 (2H, m), 3.80–4.10 (2H, m), 5.12 and 5.30 (2H, ABq, J 14.2 Hz), 5.32 (1H, s), 5.48 (1H, s), 7.25–7.55 (5H, m), 7.92 (2H, d, J 6.6 Hz), 8.13 (1H, s), and 8.67 (2H, d, J 6.6 Hz); [FAB (+ve ion) (thioglycerol) MH+ 678].

EXAMPLE 33

7β-[D-2-[(4-Ethyl-2,3-dioxopiperazin-1-yl)carbonyl amino]-2-phenylacetamido]-7α-formamido-3-[4-(pyrid-2-yl)pyridinium]methyl-ceph-3-em-4-carboxylate (a)

7β-Amino-7α-formamido-3-[4-(pyrid-2-yl)pyridinium]-methyl-ceph-3-em-4-carboxylate 7β-Amino-7α-formamidocephalosporanic acid (0.44 g; 1.39 mmol) in water (12 ml) was reacted with sodium iodide (1.84 g; 12.27 mmol) and 4-(pyrid-2-yl)pyridine (0.956 g, 6.156 mmol) as described in Example 2(a) to afford the title compound (0.22 g; 38%); $\lambda_{max}$ (H$_2$O) 263 ($\epsilon_m$ 15382), and 289 nm ($\epsilon_m$ 16785); $\nu_{max}$ (KBr) 3419, 1717, and 1635 (br) cm$^{-1}$; $\delta_H$ (D$_2$O) (major rotamer) 3.13 and 3.61 (2H, ABq, J 17.6 Hz), 5.31 and 5.39 (2H, ABq, J 14.9 Hz), 5.37 (1H, s), 7.64 (1H, ddd, J 1.1, 5.0 and 7.4 Hz), 8.0–8.2 (3H, m), 8.54 (2H, d, J 6.8 Hz), 8.75 (1H, d, J 4.3 Hz), and 9.01 (2H, d, J 6.9 Hz); [FAB (+ve ion) (thioglycerol) MH+ 412].

(b) 7β-[D-2-[(4-Ethyl-2,3-dioxopiperazin-1-yl)carbonyl amino]-2-phenylacetamido]-7α-formamido-3-[4-pyrid-2-yl)pyridinium]methyl-ceph-3-em 4-carboxylate 7β-Amino 7α-formamido-3-[4-(pyrid-2-yl)pyridinium]methyl-ceph-3-em 4-carboxylate (100 mg; 0.243 mmol) in dry dichloromethane (7 ml) containing N,N-dimethylaniline (236 mg; 1.94 mmol) and trimethylchlorosilane (158 mg; 1.56 mmol) was refluxed under argon for 50 min. Further portions of N,N-dimethylaniline (59 mg; 0.49 mmol) and trimethylchlorosilane (40 mg; 0.39 mmol) were added and the mixture refluxed for a further 30 min. The mixture was cooled to ca. 0° C. (ice/water) and a solution of D-2-[(4-ethyl-2,3-dioxopiperazin-1-yl) carbonylamino]-2-phenylacetyl chloride (freshly prepared from the corresponding acid (116 mg; 0.365 mmol) via the method in Example 1(b)) in dry dichloromethane (3 ml) added. After 2 h, the title compound (106 mg; 61%) (containing ca. 15% L isomer) was isolated as described in Example 1(c); $\lambda_{max}$ (H$_2$O) 262 ($\epsilon_m$ 14500), and 284 nm ($\epsilon_m$ 14000); $\nu_{max}$ (KBr) 3400, 3290, 1781, 1710 (sh), 1683, 1634, and 1620 (sh) cm$^{-1}$; $\delta_H$ (D$_2$O) (D isomer, major rotamer) 1.13 (3H, t, J 7.2 Hz), 2.89 and 3.48 (2H, ABq, J 17.8 Hz), 3.45 (2H, q, J 7.2 Hz), 3.55–3.75 (2H, m), 3.80–4.05 (2H, m), 5.21 and 5.44 (2H, ABq, J 15.0 Hz), 5.35 (1H, s), 5.45 (1H, s), 7.15–7.60 (5H, m), 7.60–7.70 (1H, m), 7.80–8.20 (2H, m), 8.14 (1H, s), 8.50 (2H, d, J 6.7 Hz), 8.76 (1H, d, J 4.1 Hz), and 8.94 (2H, d, J 6.7 Hz); [FAB (+ve ion) (thioglycerol) MH+ 713].

EXAMPLE 34

7β-[D-2-(3,4-Diacetoxyphenyl)-2-[(4-ethyl-2,3-dioxopiperazin-1-yl)carbonylamino]acetamido]-3-(4-ethyl pyridinium)methyl-7α-formamido-ceph-3-em-4-carboxylate 7β-Amino-3-(4-ethylpyridinium)methyl-7α-formamido-ceph-3-em-4-carboxylate (312 mg; 0.86 mmol) in dry dichloromethane (12 ml) containing N,N-dimethylaniline (836 mg; 6.90 mmol) and trimethylchlorosilane (562 mg; 5.17 mmol) was refluxed under argon for ca. 0.5 h. The resulting solution was cooled and a solution of D-2-(3,4-diacetoxyphenyl)-2-[(4-ethyl-2,3-dioxopiperazin-1-yl)carbonylamino]acetyl chloride (freshly prepared from the corresponding acid (562 mg; 1.29 mmol) via the method in Example 2(b)) in dry dichloromethane (ca. 10 ml) added with stirring at room temperature. After 1.25 h, purification as in Example 1(c) afforded the title compound (310 mg; 46%) (containing ca. 25% L isomer); $\lambda_{max}$ (H$_2$O) 252 nm ($\epsilon_m$ 17443); $\nu_{max}$ (KBr) 3411, 3285 (sh), 1772, 1710 (sh), 1682, 1636, and 1615 cm$^{-1}$; $\delta_H$ (D$_2$O) (D isomer, major rotamer) 1.17 (3H, t, J 7.2 Hz), 1.32 (3H, t, J 7.5 Hz), 2.26 (3H, s), 2.28 (3H, s), 2.75 and 3.36 (2H, ABq, J 17.4 Hz), 2.90–3.10 (2H, m), 3.49 (2H, q, J 7.2 Hz), 3.60–3.80 (2H, m), 3.80–4.10 (2H, m), 5.15 and 5.33 (2H, ABq, J 14.9 Hz), 5.34 (1H, s), 5.51 (1H, s), 7.15–7.60 (3H, m), 7.90 (2H, d, J 6 Hz), 8.15 (1H, s), and 8.67 (2H, d, J 6 Hz); [FAB (+ve ion) (thioglycerol/methanol) MH+ 780].

EXAMPLE 35

7β-[D-2-(3,4-Dihydroxyphenyl)-2-[(4-ethyl-2,3-dioxo piperazin-1-yl)carbonylamino]acetamido]-3-(4-ethyl pyridinium)methyl-7α-formamido-ceph-3-em-4-carboxylate 7β-[D-2-(3,4-Diacetoxyphenyl)-2-[(4-ethyl-2,3-dioxopiperazin-1-yl)carbonylamino]acetamido-3-(4-ethylpyridinium)methyl-7α-formamido-ceph-3-em-4-carboxylate (70 mg; 0.09 mmol) in water (10 ml) was reacted with sodium sulphite (28 mg, 0.225 mmol) as in Example 3 to afford the title compound (42 mg; 67%) (containing ca. 25% L isomer); $\lambda_{max}$ (H$_2$O) 248 nm ($\epsilon_m$ 19118); $\nu_{max}$ (KBr) 3390 (sh), 3290, 1779, 1710 (sh), 1677, 1638, and 1618 cm$^{-1}$; $\delta_H$(D$_2$O) (D isomer, major rotamer) 1.15 (3H, t, J 7.0 Hz), 1.28 (3H, t, J 7.3 Hz), 2.81 (1H, higher field half of ABq, J 17.5 Hz), 2.85–3.00 (2H, m), 3.30–3.55 (3H, m), 3.55–3.75 (2H, m), 3.80–4.10 (2H, m), 5.12 (1H, higher field half of ABq, J 14 Hz), 5.28 (1H, s, obscuring lower field arm of ABq), 5.32 (1H, s), 6.70–7.05 (3H, m), 7.75–7.95 (2H, m), 8.12 (1H, s), and 8.55–8.65 (2H, m); [FAB (+ve ion) (thioglycerol/methanol) MH+ 696].

EXAMPLE 36

Minimum Inhibitory Concentration (MIC) values of compounds of the invention against *E coli* DC 0, *K pneumoniae* T767, and *P aeruginosa* NCTC 10662 were determined by serial dilution in a nutrient agar (from Oxoid Ltd., Basingstoke, England). The plates were inoculated with $10^4$ colony forming units and incubated overnight at 37° C. The MIC values recorded in Table 1 were the lowest concentration of antibiotic to inhibit growth. Comparative data for 7α-formamido-3-(pyridiniummethyl)-7β-(thien-2-yl-acetamido)-ceph-3-em-4-carboxylate (Compound A), disclosed in European Patent Application No. 82303821.1 (Publication Number 0 071 395), are also given.

TABLE 1

| | MIC data | | |
|---|---|---|---|
| | MIC (μg/ml) | | |
| Organism | Example 3 | Example 29 | Compound A |
| *E. coli* DC 0 | 0.12 | 0.5 | 25 |
| *K. pneumoniae* T767 | 0.12 | 1 | 25 |
| *P. aeruginosa* NCTC 10662 | 1 | 8 | 50 |

We claim:

1. A compound of the formula (II):

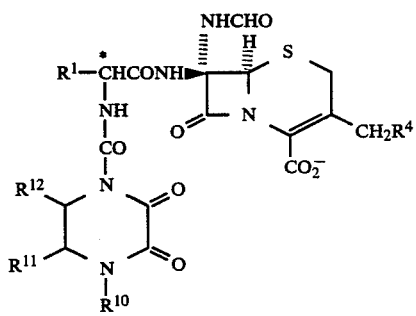

(II)

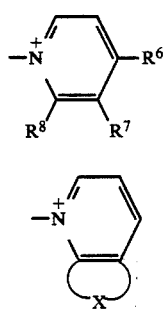

a pharmaceutically acceptable salt thereof or an in vivo hydrolyzable ester thereof wherein $R^1$ is phenyl unsubstituted or substituted with up to 3 moieties selected from the group consisting of acetoxy, hydroxy and chloro, or $R^1$ is 2-thienyl or 2-furyl; $R^4$ is a substituted pyridinium moiety of the formula (a) or (b):

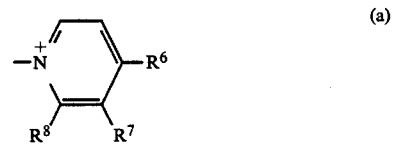
(a)

(b)

wherein one of $R^6$, $R^7$ and $R^8$ is alkyl to 1 to 6 carbon atoms; or cycloalkyl of 3 to 7 carbon atoms; and the other 2 of $R^6$, $R^7$ and $R^8$ are hydrogen; or $R^6$ is 2-pyridyl and $R^7$ and $R^8$ are hydrogen; X is —$(CH_2)_n$— wherein n is an integer having the value 2, 3 or 4; or X together with the bond in the ring to which it is joined forms a 6-membered aromatic carbocyclic ring, $R^{10}$ is alkyl of 1 to 4 carbon atoms; and $R^{11}$ and $R^{12}$ are each hydrogen.

2. A compound according to claim 1 wherein $R^1$ is phenyl, 3,4-dihydroxyphenyl, 3,4-diacetoxyphen-yl, 2-chloro-4,5-diacetoxyphenyl, 2-chloro-4,5-dihydroxyphen-yl, 2-thienyl, or 2-furyl.

3. A pharmaceutical composition useful for treating bacterial infections in humans and animals which comprises an antibacterially effective amount of a compound of formula (II):

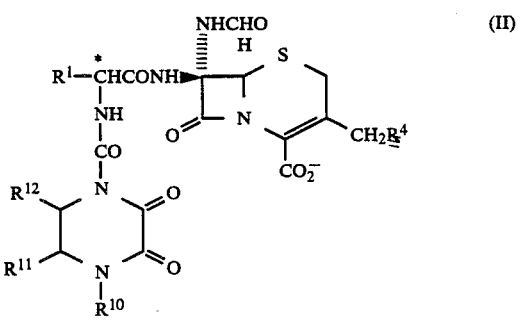

(II)

a pharmaceutically acceptable salt thereof or an in vivo hydrolyzable ester thereof wherein $R^1$ is phenyl unsubstituted or substituted with up to 3 moieties selected from the group consisting of acetoxy, hydroxy and chloro, $R^1$ is 2-thienyl or 2-furyl; $R^4$ is a substituted pyridinium moiety of the formula (a) or (b):

(a)

(b)

wherein one of $R^6$, $R^7$ and $R^8$ is alkyl of 1 to 6 carbon atoms; or cycloalkyl of 3 to 7 carbon atoms; and the other 2 of $R^6$, $R^7$ and $R^8$ are hydrogen; or $R^6$ is 2-pyridyl and $R^7$ and $R^8$ are hydrogen; X is—$(CH_2)_n$— wherein n is an integer having the value 2, 3 or 4; or X together with the bond in the ring to which it is joined forms a 6-membered aromatic carbocyclic ring, $R^{10}$ is alkyl of 1 to 4 carbon atoms; and $R^{11}$ and $R^{12}$ are each hydrogen, in combination with a pharmaceutically acceptable carrier.

4. A pharmaceutical composition according to claim 3 wherein $R^1$ is phenyl, 3,4-dihydroxy-phenyl, 3,4-diacetoxyphenyl, 2-chloro-4,5-diacetoxyphenyl, 2-chloro-4,5-dihydroxyphenyl, 2-thienyl, or 2-furyl.

5. A method of treating bacterial infections in humans and animals which comprises administering to a human or animal in need thereof an antibacterially effective amount of a compound of formula (II):

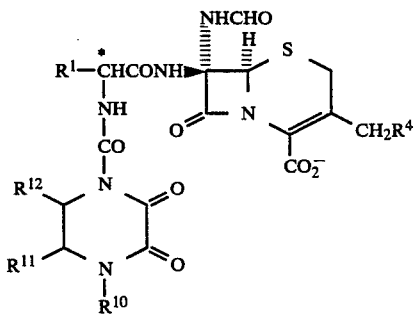

(II)

a pharmaceutically acceptable salt thereof or an in vivo hydrolyzable ester thereof wherein $R^1$ is phenyl unsubstituted or substituted with up to 3 moieties selected from the group consisting of acetoxy, hydroxy and chloro, or $R^1$ is 2-thienyl or 2-furyl; $R^4$ is a substituted pyridinium moiety of the formula (a) or (b):

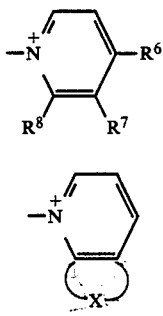

wherein one of $R^6$, $R^7$ and $R^8$ is alkyl of 1 to 6 carbon atoms; or cycloalkyl of 3 to 7 carbon atoms; and the other 2 of $R^6$, $R^7$ and $R^8$ are hydrogen; or $R^6$ is 2-pyridyl and $R^7$ and $R^8$ are hydrogen; X is—$(CH_2)_n$—wherein n is an integer having the value 2, 3 or 4; or X together with the bond in the ring to which it is joined forms a 6-membered aromatic carbocyclic ring, $R^{10}$ is alkyl of 1 to 4 carbon atoms; and $R^{11}$ and $R^{12}$ are each hydrogen.

6. A method according to claim 5 wherein $R^1$ is phenyl, 3,4-dihydroxyphenyl, 3,4-diacetoxyphenyl, 2-chloro-4,5-diacetoxyphenyl, 2-chloro-4,5-dihydroxyphenyl, 2-thienyl, or 2-furyl.

7. A pharmaceutical composition useful for treating bacterial infections in humans and animals which comprises an antibacterially effective amount of a compound of formula (II):

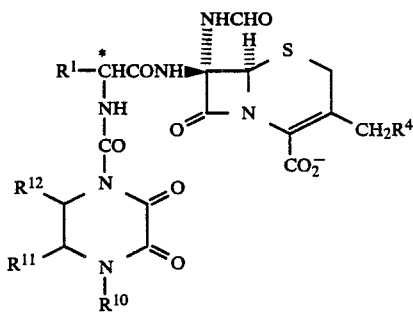

(II)

a pharmaceutically acceptable salt thereof or an in vivo hydrolyzable ester thereof wherein $R^1$ is phenyl unsubstituted or substituted with up to 3 moieties selected from the group consisting of acetoxy, hydroxy and chloro, or $R^1$ is 2-thienyl or 2-furyl; $R^4$ is a substituted pyridinium moiety of the formula (a) or (b):

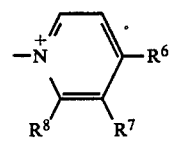

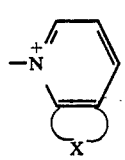

wherein one of $R^6$, $R^7$ and $R^8$ is alkyl of 1 to 6 carbon atoms; or cycloalkyl of 3 to 7 carbon atoms; and the other 2 of $R^6$, $R^7$ and $R^8$ are hydrogen; or $R^6$ is 2-pyridyl and $R^7$ and $R^8$ are hydrogen; X is—$(CH_2)_n$— wherein n is an integer having the value 2, 3 or 4; or X together with the bond in the ring to which it is joined forms a 6-membered aromatic carbocyclic ring, $R^{10}$ is alkyl of 1 to 4 carbon atoms; and $R^{11}$ and $R^{12}$ are each hydrogen, and a β-lactam inhibitory amount of a β-lactam inhibitor, in combination with a pharmaceutically acceptable carrier.

8. A pharmaceutical composition according to claim 7 wherein $R^1$ is phenyl, 3,4-dihydroxyphenyl, 3,4-diacetoxyphenyl, 2-chloro-4,5-diacetoxyphenyl, 2-chloro-4,5-dihydroxyphenyl, 2-thienyl, or 2-furyl.

9. A method of treating bacterial infections in humans and animals which comprises administering to a human or animal in need thereof an antibacterially effective amount of a compound of formula (II):

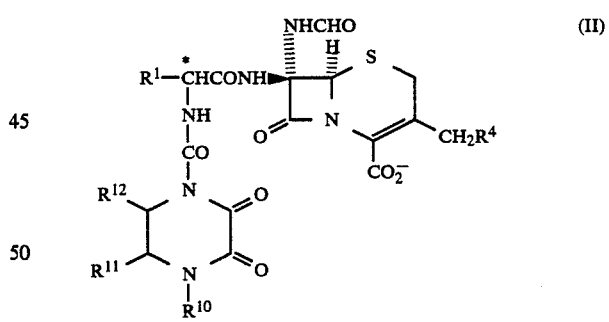

(II)

a pharmaceutically acceptable salt thereof or an in vivo hydrolyzable ester thereof wherein $R^1$ is phenyl unsubstituted or substituted with up to 3 moieties selected from the group consisting of acetoxy, hydroxy and chloro, or $R^1$ is 2-thienyl or 2-furyl; $R^4$ is a substituted pyridinium moiety of the formula (a) or (b):

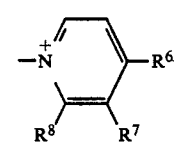

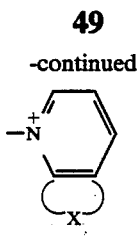

wherein one of $R^6$, $R^7$ and $R^8$ is alkyl of 1 to 6 carbon atoms; or cycloalkyl of 3 to 7 carbon atoms; and the other 2 of $R^6$, $R^7$ and $R^8$ are hydrogen; or $R^6$ is 2-pyridyl and $R^7$ and $R^8$ are hydrogen; X is—$(CH_2)_n$— wherein n is an integer having the value 2, 3 or 4; or X together with the bond in the ring to which it is joined forms a 6-membered aromatic carbocyclic ring, $R^{10}$ is alkyl of 1 to 4 carbon atoms; and $R^{11}$ and $R^{12}$ are each hydrogen, and a β-lactam inhibitory amount of a β-lactam inhibitor, in combination with a pharmaceutically acceptable carrier.

10. A method according to claim 9 wherein $R^1$ is phenyl 3,4-dihydroxyphenyl, 3,4-diacetoxyphenyl, 2-chloro-4,5-diacetoxyphenyl-2-chloro-4,5-dihydroxyphenyl, 2-thienyl, or 2-furyl.

11. A compound according to claim 1 which is selected from the group consisting of:

7β-[D-2-[(4-ethyl-2,3-dioxopiperazin-1-yl) carbonylamino]-2-phenylacetamido]-3-(4-ethylpyridinium) methyl-7α-formamido-ceph-3-em-4-carboxylate, 3-(2,3-cyclopentenopyridinium)methyl-7β-[D-2-(3,4-diacetoxyphenyl)-2-[(4-ethyl-2,3-dioxopiperazin-1-yl)carbonylamino]acetamido]-7α-formamido-ceph-3-em-4-carboxylate, 3-(2,3-cyclopentenopyridinium)methyl-7β-[D-2-(3,4-dihydroxyphenyl)-2-[(4-ethyl-2,3-dioxopiperazin-1-yl carbonylamino]acetamido]-7α-formamido-ceph-3-em-4-carboxylate, 7β-[D,L-2-[(4-ethyl-2,3-dioxopiperazin-1-yl) carbonylamino]-2-(fur-2-yl)acetamido]-7α-formamido-3-(4-ethylpyridinium)methyl-ceph-3-em-4-carboxylate, 7β-[D,L-2-[4-ethyl-2,3-dioxopiperazin-1-yl) carbonylamino]-2-(thien-2-yl)acetamido]-3-(4-ethylpyridinium)methyl-7α-formamido-ceph-3-em-4-carboxylate, 7β-[D,L-2-[(4-ethyl-2,3-dioxopiperazin-1-yl) carbonylamino]-2-(3,4-methylenedioxyphenyl)acetamido]-3-(4-ethylpyridinium)methyl-7α-formamido-ceph-3-em-4-carboxylate, 7β-[D-2-[2-chloro-4,5-diacetoxyphenyl)-2-[(4-ethyl-2,3-dioxopiperazin-1-ylcarbonylamino]acetamino]-3-(4-ethylpyridinium)methyl-7α-formamido-ceph-3-em-4-carboxylate, 7β-[D-2[(4-ethyl-2,3-dioxopiperazin-yl) carbonylamino]-2-phenylacetamido]-7α-formamido-3-(3-hydroxymethylpyridinium)methyl-ceph-3-em-4-carboxylate, 7β-[D-2-[(4-ethyl-2,3-dioxopiperazin-1-yl) carbonylamino]-2-phenylacetamido]-7α-formamido-3-(4-methylpyridinium)methyl-ceph-3-em-4carboxylate, 7β-[D-2-[(4-ethyl-2,3-dioxopiperazin-1-yl) carbonylamino]-2-phenylacetamido]-3-(3-ethyl-4-methylpyridinium)methyl-7α-formamido-ceph-3-em-4-carboxylate, 7β-[D-2-[(4-ethyl-2,3-dioxopiperazin-1-yl) carbonylamino]-2-phenylacetamido]-7α-formamido-3-[3-(3-hydroxypropyl)pyridinium]methyl-ceph-3-em-4-carboxylate, 7β-[D-2-[(4-ethyl-2,3-dioxopiperazin-1-yl) carbonylamino]-2-phenylacetamido]-7α-formamido-3-(4-phenylpyridinium]methyl-ceph-3-em-4-carboxylate, 3-(2,3-cyclohexenopyridinium)methyl-7β-[D-2-[4-ethyl-2,3-dioxopiperazin-1-yl]carbonylamino)-2-phenylacetamido]-7α-formamido-ceph-3-em-4-carboxylate, 7β-[D-2-(3,4-diacetoxyphenyl)-2-[(4-ethyl-2,3-dioxopiperazin-1-yl)carbonylamino]acetamido]-7α-formamido-3-(quinolinium)methyl-ceph-3-em-4-carboxylate, 3-[4-(tert.butyl)pyridinium]methyl-7β-[D-2-[(4-ethyl-2,3-dioxopiperazin-1-yl)carbonylamino]-2-phenylacetamido]-7α-formamido-ceph-3-em-4-carboxylate, 7β-[D-2-[(4-(3-chlorophenyl)-2,3-dioxopiperazin-1-yl) carbonylamino]-2-phenylacetamido]-3-(4-ethylpyridinium) methyl-7α-formamido-ceph-3-em-4-carboxylate, 7β-[D-2-[(4-ethyl-2,3-dioxopiperazin-1-yl)carbonylamino]-2-phenylacetamido]-7α-formamido-3-(4-methoxypyridinium) methyl-ceph-3-em-4-carboxylate, 7β-[D-2-[(4-ethyl-2,3-dioxopiperazin-1-yl)carbonylamino]-2-phenylacetamido]-7α-formamido-3-[4-(prop-1-yl)pyridinium]methyl-ceph-3-em-4-carboxylate, 7β-[D-2-[(4-ethyl-2,3-dioxopiperazin-1-yl)carbonylamino]-2-phenylacetamido]-3-(2-ethylpyridinium)methyl-7α-formamido-cept-3-em-4-carboxylate, 7β-[D-2-[(4-ethyl-2,3-dioxopiperazin-1-yl)carbonylamino]-2-phenylacetamido]-3-(3-ethylpyridinium)methyl-760 -formamido-ceph-3-em-4-carboxylate, 3-(4-cyclopropylapyridinium)methyl-7β-[D-2-[(4-ethyl-2,3-dioxopiperazin-1-yl)carbonylamino]-2-phenylacetamido]-7α-formamido-ceph-3em-4-carboxylate, 3-(4-cyclopropylpyridinium)methyl-7β-[D-2-(3,4-diacetoxyphenyl)-2-[(4-ethyl-2,3-dioxopiperazin-1yl) carbonylamino]acetamido]-7α-formamido-ceph-3-em-4-carboxylate, 3-(4-cyclopropylpyridinium)methyl-7β-[D-2-(3,4-dihydroxyphenyl-2-[(4-ethyl-2,3-dioxopiperazin-1yl) carbonylamino]acetamido]-7α-formamido-ceph-3-em-4-carboxylate, 7β-[D-2-[(4-ethyl-2,3-dioxopiperazin-1-yl)carbonylamino]-2-phenylacetamido]-7α-formamido-3-[4-(isopropyl)pyridinium]methyl-ceph-3-em-4-carboxylate, 7β-[D-2-[(4-ethyl-2,3-dioxopiperazin-1-yl)carbonylamino]-2-phenylacetamido]-7α-formamido-3-[4-pyrid-2-yl)pyridinium]methyl-ceph-3-em-4-carboxylate, 7β-[D-2-(3,4-diacetoxyphenyl)-2-[(4-ethyl-2,3-dioxopiperazin-1-yl)carbonylamino]acetamido]-3-(4-ethylpyridinium) methyl-7α-formamido-ceph-3-em-4-carboxylate, and 7β-[D-2-(3,4-dihydroxyphenyl)-2-[4-ethyl-2,3-dioxopiperazin-1-yl)carbonylamino]acetamido]-3-(4-ethylpyridinium)methyl-7α-formamido-ceph-3-em-4-carboxylate.

12. A composition according to claim 3 wherein the compound is selected from the group consisting of:

7β-[D-2-[(4-ethyl-2,3-dioxopiperazin-1-yl) carboxylamino]-2-phenylacetamido]-3-(4-ethylpyridinium)methyl-7α-formamido-ceph-3-em-4-carboxylate, 3-(2,3-cyclopentenopyridinium)methyl-7β-[D-2-(3,4-diacetoxyphenyl)-2-[(4-ethyl-2,3-dioxopiperazin-1-yl) carbonylamino]acetamido]-7α-formamido-ceph-3-em-4-carboxylate, 3-(2,3-cyclopentenopyridinium)methyl-7β-[D-2-(3,4-dihydroxyphenyl)-2-[(4-ethyl-2,3-dioxopiperazin-1yl) carbonylamino]acetamido]-7α-formamido-ceph-3-em-4-carboxylate, 7β-[D,L-2-[(4-ethyl-2,3-dioxopiperazin-1-yl) carbonylamino]-2-(fur-2-yl)acetamido]-7α-formamido-3-(4-ethylpyridinium)methyl-ceph-3-em-4-carboxylate, 7β-[D,L-2-[(4-ethyl-2,3-dioxopiperazin-1-yl) carbonylamino]-2-(thien-2-yl)acetamido]-3-(4-ethylpyridinium)methyl-7α-formamido-ceph-3-em-4-carboxylate, 7β-[D,L-2-[(4-ethyl-2,3-dioxopiperazin-1-yl) carbonylamino]-2-(3,4-methylenedioxyphenyl)acetamido]-3-(4-ethylpyridinium)methyl-7α-formamido-ceph-3-em-4-carboxylate, 7β-[D-2-[2-chloro-4,5-diacetoxyphenyl)-2-[(4-ethyl-2,3-dioxopiperazin-1-ylcarbonylamino]acetamino]-3-(4-ethylpyridinium)methyl-7α-formamido-ceph-3-em-4-carboxylate, 7β-[D-2-[(4-ethyl-2,3-dioxopiperazin-1-yl) carbonylamino]-2-phenylacetamido]-7α-formamido-3-(3-hydroxymethylpyridinium)methyl-ceph-3-em-4carboxylate, 7β-[D-2-[(4-ethyl-2,3-dioxopiperazin-1-yl) carbonylamino]-2-phenylacetamido]-7α-formamido-3-(4-methylpyridinium)methyl-ceph-3-em-4-carboxylate, 7β-[D-2-(4-ethyl-2,3-dioxopiperazin-1-yl) carbonylamino]-2-phenylacetamido]-3-(3-ethyl-4-methylpyridinium)methyl-7α-formamido-ceph-3-em-4-carboxylate, 7β-[D-2-[(4-ethyl-2,3-dioxopiperazin-1-yl) carbonylamino]-2-phenylacetamido]-7α-formamido-3-[3-(3-hydroxypropyl)pyridinium]methyl-ceph-3-em-4-carboxylate, 7β-[D-2-(4-ethyl-2,3-dioxopiperazin-1-yl) carbonylamino]-2-phenylacetamido]-7α-formamido-3-(4-phenylpyridinium]methyl-ceph-3-em-4-carboxylate, 3-(2,3-cyclohexenopyridinium)methyl-7β-[D-2-([4-ethyl-2,3-dioxopiperazin-1-yl]carbonylamino)-2-phenylacetamido]- 7α-formamido-ceph-3-em-4-carboxylate, 7β-[D-2-(3,4-diacetoxyphenyl)-2-[(4-ethyl-2,3-dioxopiperazin-1-yl)carbonylamino]acetamido]-7α-formamido-3-(quinolinium)methyl-ceph-3-em-4-carboxylate, 3-[4-(tert.-butyl)pyridinium]methyl-7β-[D-2-[(4-ethyl-2,3-dioxopiperazin-1-yl)carbonylamino]-2-phenylacetamido]-7α-formamido-ceph-3-em-4-carboxylate, 7β-[D-2-[(4-(3-chlorophenyl)-2,3-dioxopiperazin-1-yl) carbonylamino]-2-phenylacetamido]-3-(4-ethylpyridinium) methyl-7α-formamido-ceph-3-em-4-carboxylate, 7β-[D-2-[(4-ethyl-2,3-dioxopiperazin-1-yl)carbonylamino]-2-phenylacetamido]-7α-formamido-3-(4-methoxypyridinium) methyl-ceph-3-em-4-carboxylate, 7β-[D-2-[(4-ethyl-2,3-dioxopiperazin-1-yl)carbonylamino]-2-phenylacetamido]-7α-formamido-3-[4-prop-1-yl)pyridinium]methyl-ceph-3-em-4-carboxylate, 7β-[D-2-[(4-ethyl-2,3-dioxopiperazin-1-yl)carbonylamino]-2-phenylacetamido]-3-(2-ethylpyridinium)methyl-7α-formamido-ceph-3-em-4-carboxylate, 7β-[D-2-[(4-ethyl-2,3-dioxopiperazin-1-yl)carbonylamino]-2-phenylacetamido]-3-(3-ethylpyridinium)methyl-7α-formamido-ceph-3-em-4-carboxylate, 3-(4-cyclopropylpyridinium)methyl-7β-[D-2-[(4-ethyl-2,3-dioxopiperazin-1-yl)carbonylamino]-2-phenylacetamido]-7α-formamido-ceph-3-em-4-carboxylate, 3-(4-cyclopropylpyridinium)methyl-7β-[D-2-(3,4-diacetoxyphenyl)-2-[(4-ethyl-2,3-dioxopiperazin-1-yl) carbonylamino]acetamido]-7α-formamido-ceph-3-em-4-carboxylate, 3-(4-cyclopropylpyridinium)methyl-7β-[D-2-(3,4-dihydroxyphenyl)-2-[(4-ethyl-2,3-dioxopiperazin-1-yl) carbonylamino]acetamido]-7α-formamido-ceph-3-em-4-carboxylate, 7β-[D-2-[(4-ethyl-2,3-dioxopiperazin-1-yl)carbonylamino]-2-phenylacetamido]-7α-formamido-3-[4-(isopropyl)pyridinium]methyl-ceph-3-em-4-carboxylate, 7β-[D-2-[(4-ethyl-2,3-dioxopiperazin-1-yl)carbonylamino]-2-phenylacetamido]-7α-formamido-3[4-pyrid-2yl)pyridinium]methyl-ceph-3-em-4-carboxylate, 7β-[D-2-(3,4-diacetoxyphenyl)-2-[(4-ethyl-2,3-dioxopiperazin-1-yl)carbonylamino]acetamido]-3-(4-ethylpyridinium)methyl-7α-formamido-ceph-3-em-4-carboxylate, and 7β-[D-2-(3,4-dihydroxyphenyl)-2-[4-ethyl-2,3-dioxopiperazin-1-yl)carbonylamino]acetamido]-3-(4-ethylpyridinium)methyl-7α-formamido-ceph-3-em-4-carboxylate.

13. A method according to claim 5 wherein the compound is selected from the group consisting of:

7β-[D-2-[(4-ethyl-2,3-dioxopiperazin-1-yl) carbonylamino]-2-phenylacetamido]-3-(4-ethylpyridinium) methyl-7α-formamido-ceph-3-em-4-carboxylate, 3-(2,3-cyclopentenopyridinium)methyl-7β-[D-2-(3,4-diacetoxyphenyl)-2-[(4-ethyl-2,3-dioxopiperazin-1-yl) carbonylamino]acetamido]-7α-formamido-ceph-3-em-4-carboxylate, 3-(2,3-cyclopentenopyridinium)methyl-7β-[D-2-(3,4-dihydroxyphenyl)-2-[(4-ethyl-2,3-dioxopiperazin-1-yl) carbonylamino]acetamido]-7α-formamido-ceph-3-em-4-carboxylate, 7β-[D,L-2-[(4-ethyl-2,3-dioxopiperazin-1-yl) carbonylamino]-2-(fur-2-yl)acetamido]-7α-formamido-3-(4-ethylpyridinium)methyl-ceph-3-em-4-carboxylate, 7β-[D,L-2-[(4-ethyl-2,3-dioxopiperazin-1-yl) carbonylamino]-2-(thien-2-yl)acetamido]-3-(4-ethylpyridinium)methyl-7α-formamido-ceph-3-em-4-carboxylate, 7β-[D,L-2-[(4-ethyl-2,3-dioxopiperazin-1-yl) carbonylamino]-2-(3,4-methylenedioxyphenyl)acetamido]-3-(4-ethylpyridinium)methyl-7α-formamido-ceph-3-em-4-carboxylate, 7β-[D-2-[2-chloro-4,5-diacetoxyphenyl)-2-[(4-ethyl-2,3-dioxopiperazin-1-ylcarbonylamino]acetamino]-3-(4-ethylpyridinium)methyl-7α-formamido-ceph-3-em-4-carboxylate, 7β-[D-2-[(4-ethyl-2,3-dioxopiperazin-1-yl) carbonylamino]-2-phenylacetamido]-7α-formamido-3-

(3-hydroxymethylpyridinium)methyl-ceph-3-em-4-carboxylate,

7β-[D-2-[(4-ethyl-2,3-dioxopiperazin-1-yl) carbonylamino]-2-phenylacetamido]-7α-formamido-3-(4-methylpyridinium)methyl-ceph-3-em-4-carboxylate, 7β-[D-2-[(4-ethyl-2,3-dioxopiperazin-1-yl) carbonylamino]-2-phenylacetamido]-3-(3-ethyl-4-methylpyridinium)methyl-7α-fomamido-ceph-3-em-4-carboxylate, 7β-[D-2-[(4-ethyl-2,3-dioxopiperazin-1-yl) carbonylamino]-2-phenylacetamido]-7α-formamido-3-[3-(3-hydroxypropyl)pyridinium]methyl-ceph-3-em-4-carboxylate, 7β-[D-2-[(4-ethyl-2,3-dioxopiperazin-1-yl) carbonylamino]-2-phenylacetamido]-7α-formamido-3-(4-phenylpyridinium]methyl-ceph-3-em-4-carboxylate, 3-(2,3-cyclohexenopyridinium)methyl-7β-[D-2-([4-ethyl-2,3-dioxopiperazin-1-yl]carbonylamino)-2-phenylacetamido]-7α-formamido-ceph-3-em-4-carboxylate, 7β-[D-2-(3,4-diacetoxyphenyl)-2-[(4-ethyl-2,3-dioxopiperazin-1-yl)carbonylamino]acetamido]-7α-formamido-3-(quinolinium)methyl-ceph-3-em-4-carboxylate, 3-[4-(tert.-butyl)pyridinium]methyl-7β-[D-2-[(4-ethyl-2,3-dioxopiperazin-1-yl)carbonylamino]-2-phenylacetamido]-7α-formamido-ceph-3-em-4-carboxylate, 7β-[D-2-[(4-(3-chlorophenyl)-2,3-dioxopiperazin-1-yl)carbonylamino]-2-phenylacetamido]-3-(4-ethylpyridinium) methyl-7α-formamido-ceph-3-em-4-carboxylate, 7β-[D-2-[(4-ethyl-2,3-dioxopiperazin-1-yl)carbonylamino]-2-phenylacetamido]-7α-formamido-3-(4-methoxypyridinium) methyl-ceph-3-em-4-carboxylate, 7β-[D-2-[(4-ethyl-2,3-dioxopiperazin-1-yl)carbonylamino]-2-phenylacetamido]-7α-formamido-3-[4-(prop-1-yl)pyridinium]methyl-ceph-3-em-4-carboxylate, 7β-[D-2-[(4-ethyl-2,3-dioxopiperazin-1-yl)carbonylamino]-2-phenylacetamido]-3-(2-ethylpyridinium)methyl-7α-formamido-ceph-3-em-4-carboxylate, 7β-[D-2-[(4-ethyl-2,3-dioxopiperazin-1-yl)carbonylamino]-2-phenylacetamido]-3-(3-ethylpyridinium)methyl-7α-formamido-ceph-3-em-4-carboxylate, 3-(4-cyclopropylpyridinium)methyl-7β-[D-2-[(4-ethyl-2,3-dioxopiperazin-1-yl)carbonylamino]-2-phenylacetamido]-7α-formamido-ceph-3-em-4-carboxylate, 3-(4-cyclopropylpyridinium)methyl-7β-[D-2-(3,4-diacetoxyphenyl)-2-[(4-ethyl-2,3-dioxopiperazin-1-yl)carbonylamino]acetamido]-7α-formamido-ceph-3-em-4-carboxylate, 3-(4-cyclopropylpyridinium)methyl-7β-[D-2-(3,4-dihydroxyphenyl)-2-[(4-ethyl-2,3-dioxopiperazin-1-yl)carbonylamino]acetamido]-7α-formamido-ceph-3-em-4-carboxylate, 7β-[D-2-[(4-ethyl-2,3-dioxopiperazin-1-yl)carbonylamino]-2-phenylacetamido]-7α-formamido-3[4-(isopropyl)pyridinium]methyl-ceph-3-em-4-carboxylate, 7β-[D-2-[(4-ethyl-2,3-dioxopiperazin-1-yl)carbonylamino]-2-phenylacetamido]-7α-formamido-3-[4-pyrid-2-yl)pyridinium]methyl-ceph-3-em-4-carboxylate, 7β-[D-2-(3,4-diacetoxyphenyl)-2-[(4-ethyl-2,3-dioxopiperazin-1-yl)carbonylamino]acetamido]-3-(4-ethylpyridinium) methyl-7α-formamido-ceph-3-em-4-carboxylate, and 7β-[D-2-(3,4-dihydroxyphenyl)-2-[4-ethyl-2,3-dioxopiperazin-1-yl)carbonylamino]-3-(4-ethylpyridinium)methyl-7α-formamido-ceph-3-em-4-carboxylate.

14. A composition according to claim 7 wherein the compound is selected from the group consisting of:

7β-[D-2-[(4-ethyl-2,3-dioxopiperazin-1-yl) carbonylamino]-2-phenylacetamido]-3-(4-ethylpyridinium) methyl-7α-formamido-ceph-3-em-4-carboxylate, 3-(2,3-cyclopentenopyridinium)methyl-7α-[D-2-(3,4-diacetoxyphenyl)-2-[(4-ethyl-2,3-dioxopiperazin-1-yl)carbonylamino]acetamido]-7α-formamido-ceph-3-em-4-carboxylate, 3-(2,3-cyclopentenopyridinium)methyl-7β-[D-2-(3,4-dihydroxyphenyl)-2-[(4-ethyl-2,3-dioxopiperazin-1-yl) carbonylamino]acetamido]-7α-formamido-ceph-3-em-4-carboxylate, 7β-[D,L-2-[(4-ethyl-2,3-dioxopiperazin-1-yl) carbonylamino]-2-(fur-2-yl)acetamido]-7α-formamido-3-(4-ethylpyridinium)methyl-ceph-3-em-4-carboxylate, 7β-[D,L-2-[(4-ethyl-2,3-dioxopiperazin-1-yl) carbonylamino]-2-(thien-2-yl)acetamido]-3-(4-ethylpyridinium)methyl-7α-formamido-ceph-3-em-4-carboxylate, 7β-[D,L-2-[(4-ethyl-2,3-dioxopiperazin-1-yl) carbonylamino]-2-(3,4-methylenedioxyphenyl)acetamido]-3-(4-ethylpyridinium)methyl-7α-formamido-ceph-3-em-4-carboxylate, 7β-[D-2-[2-chloro-4,5-diacetoxyphenyl)-2-[(4-ethyl-2,3-dioxopiperazin-1-ylcarbonylamino]acetamino]-3-(4-ethylpyridinium)methyl-7α-formamido-ceph-3-em-4-carboxylate, 7β-[D-2-](4-ethyl-2,3-dioxopiperazin-1-yl) carbonylamino]-2-phenylacetamido]-7α-formamido-3-(3-hydroxymethylpyridinium)methyl-ceph-3-em-4-carboxylate, 7β-[D-2-[(4-ethyl-2,3-dioxopiperazin-1-yl) carbonylamino]-2-phenylacetamido]-7α-formamido-3-(4-methylpyridinium)methyl-ceph-3-em-4-carboxylate, 7β-[D-2-[(4-ethyl-2,3-dioxopiperazin-1-yl) carbonylamino]-2-phenylacetamido]-3-(3-ethyl-4-methylpyridinium)methyl-7α-formamido-ceph-3-em-4-carboxylate, 7β-[D-2-[(4-ethyl-2,3-dioxopiperazin-1-yl) carbonylamino]-2-phenylacetamido]-7α-formamido-3-[3-(3-hydroxypropyl)pyridinium]methyl-ceph-3-em-4-carboxylate, 7β-[D-2-[(4-ethyl-2,3-dioxopiperazin-1-yl) carbonylamino]-2-phenylacetamido]-7α-formamido-3-(4-phenylpyridinium]methyl-ceph-3-em-4-carboxylate, 3-(2,3-cyclohexenopyridinium)methyl-7β-[D-2-([4-ethyl-2,3-dioxopiperazin-1-yl]carbonylamino)-2-phenylacetamido]-7α-formamido-ceph-3-em-4-carboxylate, 7β-[D-2-(3,4-diacetoxyphenyl)-2-[(4-ethyl-2,3-dioxopiperazin-1-yl)carbonylamino]acetamido]-7α-formamido-3-(quinolinium)methyl-ceph-3-em-4carboxylate, 3-[4-(tert.-butyl)pyridinium]methyl-7β-[D-2-[(4-ethyl-2,3-dioxopiperazin-1-yl)carbonylamino]-2-phenylacetamido]-7α-formamido-ceph-3-em-4-carboxylate, 7β-[D-2-[(4-(3-chlorophenyl)-2,3-dioxopiperazin-1-yl)carbonylamino]-2-phenylacetamido-3-(4-ethylpyridinium) methyl-7α-formamido-ceph-3-em-4-carboxylate, 7β-[D-2-[(4-ethyl-2,3-dioxopiperazin-1-yl)carbonylamino]-2-phenylacetamido]-7α-formamido-3-(4-methoxypyridinium) methyl-ceph-3-em-4-carboxylate, 7β-[D-2-[(4-ethyl-2,3-dioxopiperazin-1-yl)carbonylamino[-2-phenylacetamido]-7α-formamido-3-[4-(prop-1-yl)pyridinium]methyl-ceph-3-em-4-carboxylate, 7β-[D-2-[(4-ethyl-2,3-dioxopiperazin-1-yl)carbonylamino]-2-phenylacetamido]-3-(2-ethylpyridinium)methyl-7α-formamido-ceph-3-em-4-carboxylate, 7β-[D-2-[(4-ethyl-2,3-dioxopiperazin-1-yl)carbonylamino]-2-phenylacetamido]-3-(3-ethylpyridinium)methyl-7α-formamido-ceph-3-em-4-carboxylate, 3-(4-cyclopropylpyridinium)methyl-7β-[D-2-[(4-ethyl-2,3-dioxopiperazin-1-yl)carbonylamino]-2-phenylacetamido]-7α -formamido-ceph-3-em-4-carboxylate, 3-(4-cyclopropylpyridinium)methyl-7β-[D-2-(3,4-diacetoxyphenyl)-2-[(4-ethyl-2,3-dioxopiperazin-1-yl)carbonylamino]acetamido]-7α-formamido-ceph-3-em-4-carboxylate, 3-(4-cyclopropylpyridinium)methyl-7β-[D-2-(3,4-dihydroxyphenyl)-2-[(4-ethyl-2,3-dioxopiperazin-1-yl)carbonylamino]acetamido]-7α-formamido-ceph-3-em-4-carboxylate, 7β-[D-2-[(4-ethyl-2,3-dioxopiperazin-1-yl)carbonylamino]-2-phenylacetamido]-7α-formamido-3-[4-(isopropyl)pyridinium]methyl-ceph-3-em-4-carboxylate, 7β-[D-2-[(4-ethyl-2,3-dioxopiperazin-1-yl)carbonylamino]-2-phenylacetamido]-7α-formamido-3-[4-pyrid-2-yl)pyridinium]methyl-ceph-3-em-4-carboxylate, 7β-[D-2-(3,4-diacetoxyphenyl)-2-[(4-ethyl-2,3-dioxopiperazin-1-yl)carbonylamino]acetamido]-3-(4-ethylpyridinium)methyl-7α-formamido-ceph-3-em-4-carboxylate, and 7β-[D-2-(3,4-dihydroxyphenyl)-2-[4-ethyl-2,3-dioxopiperazin-1-yl)carbonylamino]acetamido]-3-(4-ethylpyridinium)methyl-7α-formamido-ceph-3-em-4-carboxylate.

15. A method according to claim 9 wherein the compound is selected from the group consisting of:

7β-[D-2-[(4-ethyl-2,3-dioxopiperazin-1-yl) carbonylamino]-2-phenylacetamido]-3-(4-ethylpyridinium) methyl-7α-formamido-ceph-3-em-4-carboxylate, 3-(2,3-cyclopentenopyridinium)methyl-7α-[D-2-(3,4-diacetoxyphenyl)-2-[(4-ethyl-2,3-dioxopiperazin-1-yl) carbonylamino]acetamido]-7α-formamido-ceph-3-em-4-carboxylate, 3-(2,3-cyclopentenopyridinium)methyl-7β-[D-2-(3,4-dihydroxyphenyl)-2-[(4-ethyl-2,3-dioxopiperazin-1-yl) carbonylamino]acetamido]-7α-formamido-ceph-3-em-4-carboxylate, 7β-[D,L-2-[(4-ethyl-2,3-dioxopiperazin-1-yl) carbonylamino]-2-(fur-2-yl)acetamido]-7α-formamido-3-(4-ethylpyridinium)methyl-ceph-3-em-4-carboxylate, 7β-[D,L-2-[(4-ethyl-2,3-dioxopiperazin-1-yl) carbonylamino]-2-(thien-2-yl)acetamido]-3-(4-ethylpyridinium)methyl-7α-formamido-ceph-3-em-4-carboxylate, 7β-[D,L-2-[(4-ethyl-2,3-dioxopiperazin-1-yl) carbonylamino]-2-(3,4-methylenedioxyphenyl)acetamido]-3-(4-ethylpyridinium)methyl-7α-formamido-ceph-3-em-4-carboxylate, 7β-[D-2-[2-chloro-4,5-diacetoxyphenyl)-2-](4-ethyl-2,3-dioxopiperazin-1-ylcarbonylamino]acetamino]-3-(4-ethylpyridinium)methyl-7α- formamido-ceph-3-em-4-carboxylate, 7β-[D-2-[(4-ethyl-2,3-dioxopiperazin-1-yl) carbonylamino]-2-phenylacetamido]-7α-formamido-3-(3-hydroxymethylpyridinium)methyl-ceph-3-em-4-carboxylate, 7β-[D-2-[(4-ethyl-2,3-dioxopiperazin-1-yl) carbonylamino]-2-phenylacetamido]-7α-formamido-3-(4-methylpyridinium)methyl-ceph-3-em-4-carboxylate, 7β-[D-2-[(4-ethyl-2,3-dioxopiperazin-1-yl) carbonylamino]-2-phenylacetamido]-3-(3-ethyl-4-methylpyridinium)methyl-7α-formamido-ceph-3-em-4-carboxylate, 7β-[D-2-[(4-ethyl-2,3-dioxopiperazin-1-yl) carbonylamino]-2-phenylacetamido]-7α-formamido-3-]3-(3-hydroxypropyl)pyridinium]methyl-ceph-3-em-4-carboxylate, 7β-[D-2-[(4-ethyl-2,3-dioxopiperazin-1-yl) carbonylamino]-2-phenylacetamido]-7α-formamido-3-(4-phenylpyridinium]methyl-ceph-3-em-4-carboxylate, 3-(2,3-cyclohexenopyridinium)methyl-7β-[D-2-(4-ethyl-2,3-dioxopiperazin-1-yl]carbonylamino)-2-phenylacetamido]-7α-formamido-ceph-3-em-4-carboxylate, 7β-[D-2-(3,4-diacetoxyphenyl)-2-[(4-ethyl-2,3-dioxopiperazin-1-yl)carbonylamino]acetamido]-7α-formamido-3-(quinolinium)methyl-ceph-3-em-4-carboxylate, 3-[4-(tert.-butyl)pyridinium]methyl-7β-[D-2-[(4-ethyl-2,3-dioxopiperazin-1-yl)carbonylamino]-2-phenylacetamido]-7α-formamido-ceph-3-em-4-carboxylate, 7β-[D-2-[(4-(3-chlorophenyl)-2,3-dioxopiperazin-1-yl)carbonylamino]-2-phenylacetamido]-3-(4-ethylpyridinium) methyl-7α-formamido-ceph-3-em-4-carboxylate, 7β-[D-2-[(4-ethyl-2,3-dioxopiperazin-1-yl)carbonylamino]-2-phenylacetamido]-7α-formamido-3-(4-methoxypyridinium) methyl-ceph-3-em-4-carboxylate, 7β-[D-2-[(4-ethyl-2,3-dioxopiperazin-1-yl)carbonylamino]-2-phenylacetamido]-7α-formamido-3-[4-(prop-1yl)pyridinium]methyl-ceph-3-em-4-carboxylate, 7β-[D-2-[(4-ethyl-2,3-dioxopiperazin-1-yl)carbonylamino]-2-phenylacetamido]-3-(2-ethylpyridinium)methyl-7α-formamido-ceph-3-em-4-carboxylate, 7β-[D-2-[(4-ethyl-2,3-dioxopiperazin-1-yl)carbonylamino]-2-phenylacetamido]-3-(3-ethylpyridinium)methyl-7α-formamido-ceph-3-em-4-carboxylate, 3-(4-cyclopropylpyridinium)methyl-7β-[D-2-[(4-ethyl-2,3-dioxopiperazin-1-yl)carbonylamino]-2-phenylacetamido]-7α-formamido-ceph-3-em-4-carboxylate, 3-(4-cyclopropylpyridinium)methyl-7β-[D-2-(3,4-diacetoxyphenyl)-2-[(4-ethyl-2,3-dioxopiperazin-1yl)-carbonylamino]acetamido]-7α-formamido-ceph-3-em-4-carboxylate, 3-(4-cyclopropylpyridinium)methyl-7β-[D-2-(3,4-dihydroxyphenyl)-2-[(4-ethyl-2,3-dioxopiperazin-1- yl)carbonylamino]acetamido]-7α-formamido-ceph-3-em-4-carboxylate,

7β-[D-2-[(4-ethyl-2,3-dioxopiperazin-1-yl)carbonylamino]-2-phenylacetamido]-7α-formamido-3-[4-isopropyl)pyridinium]methyl-ceph-3-em-4-carboxylate, 7β-[D-2-[(4-ethyl-2,3-dioxopiperazin-1-yl)carbonylamino]-2-phenylacetamido]-7α-formamido-3-[4-pyrid-2-yl)pyridinium]methyl-ceph-3-em-4-carboxylate, 7β-[D-2-(3,4-diacetoxyphenyl)-2-[(4-ethyl-2,3-dioxopiperazin-1-yl)carbonylamino]acetamido]-3-(4-ethylpyridinium)methyl-7α-formamido-ceph-3-em-4-carboxylate, and 7β-[D-2-(3,4-dihydroxyphenyl)-2-[(4-ethyl-2,3-dioxopiperazin-1-yl)carbonylamino]acetamido]-3-(4-ethylpyridinium)methyl-7α-formamido-ceph-3-em-4-carboxylate.

* * * * *